US012338486B2

(12) United States Patent
DiIorio et al.

(10) Patent No.: US 12,338,486 B2
(45) Date of Patent: Jun. 24, 2025

(54) SINGLE-STRANDED BREAK DETECTION IN DOUBLE-STRANDED DNA

(71) Applicants: MASSACHUSETTS INSTITUTE OF TECHNOLOGY, Cambridge, MA (US); THE BROAD INSTITUTE, INC., Cambridge, MA (US)

(72) Inventors: Sarah DiIorio, Cambridge, MA (US); Joshua Elacqua, Cambridge, MA (US); Arnaud Gutierrez, Cambridge, MA (US); Navpreet Ranu, Cambridge, MA (US); Paul Blainey, Cambridge, MA (US)

(73) Assignees: MASSACHUSETTS INSTITUTE OF TECHNOLOGY, Cambridge, MA (US); THE BROAD INSTITUTE, INC., Cambridge, MA (US)

(*) Notice: Subject to any disclaimer, the term of this patent is extended or adjusted under 35 U.S.C. 154(b) by 1284 days.

(21) Appl. No.: 17/048,227

(22) PCT Filed: Apr. 18, 2019

(86) PCT No.: PCT/US2019/028091
§ 371 (c)(1),
(2) Date: Oct. 16, 2020

(87) PCT Pub. No.: WO2019/204585
PCT Pub. Date: Oct. 24, 2019

(65) Prior Publication Data
US 2021/0071240 A1 Mar. 11, 2021

Related U.S. Application Data

(60) Provisional application No. 62/660,028, filed on Apr. 19, 2018.

(51) Int. Cl.
| | | |
|---|---|---|
| *C12Q 1/6806* | (2018.01) | |
| *C12Q 1/6827* | (2018.01) | |
| *C12Q 1/6844* | (2018.01) | |
| *C12Q 1/6876* | (2018.01) | |

(52) U.S. Cl.
CPC ......... *C12Q 1/6806* (2013.01); *C12Q 1/6827* (2013.01); *C12Q 1/6876* (2013.01); *C12N 2310/20* (2017.05); *C12Q 1/6844* (2013.01); *C12Q 2600/106* (2013.01); *C12Q 2600/156* (2013.01)

(58) Field of Classification Search
CPC ... C12Q 1/6806; C12Q 1/6827; C12Q 1/6844
See application file for complete search history.

(56) References Cited

FOREIGN PATENT DOCUMENTS

WO 2004042078 A1 5/2004

OTHER PUBLICATIONS

International Search Report dated Oct. 29, 2020 for related Application No. PCT/US19/28091.
Rasila, S. et al. Critical evaluation of random mutagenesis by error-prone polymerase chain reaction protocols, *Escherichia coli* mutator strain, and hydroxylamine treament, vol. 38 No. May 1, 2009.
Yang et al. Enzymatic incorporation of a third nucleobase pair, vol. 35, No. 13. Jun. 18, 2007.
Baranello, L. et al. Mapping DNA Breaks by Next-Generation Sequencing. Oct. 17, 2017.
Matray, T. et al. A Specific Partner for Abasic Damage in DNA. Jun. 17, 1999.
Sampson, T. Exploiting CRISPR/Cas systems for biotechnology, vol. 6, No. 1. Jan. 10, 2014.
Extended European Search Report in corresponding application No. 19789196.3 dated Jan. 4, 2022.
Hill, F. et al. Comparative mutagenicities of N6-methoxy-2,6-diaminopurine and N6-methoxyaminopurine 2'-deoxyribonucleosides and their 5'-triphosphates, Jan. 1998.
Examination Report in corresponding EP application No. 19789196.3 dated Mar. 13, 2023.
Baranello, et al. "DNA Break Mapping Reveals Topoisomerase II Activity Genome-Wide" International Journal of Molecular Science, Jul. 23, 2014 (Jul. 23, 2014) vol. 15, No. 7, pp. 13111-13122.
Hill, et al. "Polymerase recognition of synthetic oligodeoxyribonucleotides incorporating degenerate pyrimidine and purine bases", Apr. 1998 (Apr. 1998) vol. 95, No. 8, pp. 4258-4263.
International Search Report dated Aug. 23, 2019 for related Application No. PCT/US19/28091.

*Primary Examiner* — Richard A Schnizer
(74) *Attorney, Agent, or Firm* — Day Pitney LLP; Christopher R. Cowles; Erica A. Fishel

(57) ABSTRACT

The present disclosure relates to compositions and methods for detection of single-stranded breaks (SSBs) in dsDNA, including in genomic DNA. Measurement of the precise location of SSB damage in DNA, e.g., genomic DNA, is provided, and involves an approach that is compatible with next-generation sequencing.

20 Claims, 25 Drawing Sheets

Specification includes a Sequence Listing.

P-A : P-G      K-T : K-C
60:40           85:15

SINGLE-STRANDED BREAK DETECTION IN DOUBLE-STRANDED DNA

CROSS-REFERENCE TO RELATED APPLICATIONS

This application is a national stage application, filed under 35 U.S.C. § 371, of International Patent Application No. PCT/US19/28091, filed Apr. 18, 2019, entitled "Single-Stranded Break Detection in Double-Stranded DNA" and published Oct. 24, 2019 as WO 2019/204585, which claims the benefit of priority under 35 U.S.C. § 119 (e) to U.S. Provisional Application No. 62/660,028, filed on Apr. 19, 2018, entitled, "Single-Stranded Break Detection in Double-Stranded DNA." The entire contents of these patent applications are hereby incorporated by reference herein.

STATEMENT REGARDING FEDERALLY SPONSORED RESEARCH

This invention was made with government support under Grant No. 2RMIHG006193 awarded by the National Institutes of Health. The government has certain rights in the invention.

FIELD OF THE INVENTION

The invention relates generally to methods and compositions for the detection of single stranded breaks in double-stranded DNA (dsDNA), e.g., genomic DNA.

BACKGROUND OF THE INVENTION

Genomic DNA is continuously in a state of damage and repair due to both internal and external sources. Single stranded breaks (SSBs) are the most common form of damage at an estimated 10,000 per cell per day from sources such as oxidative stress and through the repair machinery itself. There are direct correlations between SSB accumulation and disease, but it is unknown how the location and amount of damage relate to health outcomes. Further, certain gene editing technologies are reliant on SSBs generation at the targeted site of alteration, but it is difficult to identify locations of unintended enzyme activity. Although sequencing enables the identification of key mutations that arise through the lifetime of a cell, there are, to date, no robust methods that allow identification and quantification of SSB locations across the genome. A need therefore exists for improved compositions and methods for identifying single-stranded breaks in dsDNA, e.g., genomic DNA.

BRIEF SUMMARY OF THE INVENTION

The current disclosure relates, at least in part, to compositions and methods for detection of single-stranded breaks (SSBs) in dsDNA, including in genomic DNA. Measurement of the precise location of SSB damage in DNA, e.g., genomic DNA, is provided, via approaches that are compatible with next-generation sequencing.

In one aspect, the instant disclosure provides a composition for performing nick translation that includes a DNA polymerase and a nucleotide analog that possesses the ability to base pair with at least two of the nucleotide bases adenine, guanine, cytosine and thymine.

In one embodiment, the nucleotide analog is dPTP, dKTP or dRTP.

In another embodiment, the composition includes two or more nucleotide analogs. Optionally, the two or more nucleotide analogs include dPTP and dKTP or dPTP and dRTP.

In certain embodiments, the DNA polymerase is a DNA polymerase I.

In some embodiments, the DNA polymerase is Taq DNA polymerase, Therminator DNA polymerase or *Sulfolobus* DNA polymerase IV.

An additional aspect of the instant disclosure provides a method for identifying the presence and position of a single-stranded break within a double-stranded nucleic acid, the method involving: obtaining a sample having a double-stranded nucleic acid; contacting the sample with DNA polymerase and a nucleotide analog that possesses the ability to base pair with at least two of the nucleotide bases adenine, guanine, cytosine and thymine, under conditions that allow for DNA polymerase extension and incorporation of the nucleotide analog to occur; contacting the sample with a tagged nucleotide and natural deoxyribonucleotides under conditions that allow for DNA polymerase extension and incorporation of the tagged nucleotide and natural deoxyribonucleotides to occur; fragmenting the double-stranded nucleic acid in the sample, thereby producing a population of double-stranded nucleic acid fragments; isolating double-stranded nucleic acid fragments having the tagged nucleotide from the population of double-stranded nucleic acid fragments; ligating an exogenous oligonucleotide sequence to the double-stranded nucleic acid fragments; amplifying the isolated double-stranded nucleic acid fragments having the exogenous oligonucleotide sequence, thereby forming an amplified population of isolated double-stranded nucleic acid fragments; identifying the sequence of the amplified population of isolated double-stranded nucleic acid fragments; and within a sequence obtained from the amplified population of isolated double-stranded nucleic acid fragments, identifying a series of three or more consecutive nucleotide positions that have at least two or more detectable nucleotide residues present at a level of at least 10% of all nucleotide residues detected at that position, at each of the three or more consecutive nucleotide positions, thereby identifying the presence and position of a single-stranded break within a double stranded nucleic acid.

In one embodiment, the nucleotide analog is dPTP, dKTP, dRTP, inosine, 3-Nitropyrrole, 5-nitroindole, 3-methyl isocarbostyril (MICS), 5-methyl isocarbostyril (5MICS) and/or 3-methyl 7-propynyl isocarbostyril (PIM), optionally where the nucleotide analog is dPTP, dKTP, and/or dRTP.

In another embodiment, the sample is contacted with two or more nucleotide analogs that each possesses the ability to base pair with at least two of the nucleotide bases adenine, guanine, cytosine and thymine, optionally where the two or more nucleotide analogs include dPTP and dKTP or dPTP and dRTP.

In certain embodiments, the tagged nucleotide is a biotin-labeled nucleotide or a desthiobiotin-labeled nucleotide. In a related embodiment, the isolating step includes contacting double-stranded nucleic acid fragments that have incorporated the biotin-labeled or desthiobiotin-labeled nucleotides with streptavidin, optionally where the streptavidin is attached to a solid support, optionally where the solid support is a bead, optionally where the isolating step further involves centrifugation of the solid support.

In one embodiment, the fragmenting step produces a population of double-stranded nucleic acid fragments having an average fragment size of 20-2000 base pairs, optionally the fragmenting step produces a population of double-stranded nucleic acid fragments having an average fragment size of 100-1000 base pairs, optionally the fragmenting step produces a population of double-stranded nucleic acid fragments having an average fragment size of 200-700 base pairs.

In some embodiments, the sample having the double-stranded nucleic acid includes a prokaryotic double-stranded nucleic acid, optionally a prokaryotic double-stranded nucleic acid genome.

In other embodiments, the sample having the double-stranded nucleic acid includes a eukaryotic double-stranded nucleic acid, optionally a mammalian genome, optionally a mammalian genome that has been subjected to a CRISPR/Cas9 procedure.

In some embodiments, the DNA polymerase of the step of contacting the sample with a tagged nucleotide and natural deoxyribonucleotides under conditions that allow for DNA polymerase extension and incorporation of the tagged nucleotide and natural deoxyribonucleotides to occur is *E. coli* DNA polymerase. Optionally the *E. coli* DNA polymerase is a different DNA polymerase from the DNA polymerase employed for the step of contacting the sample with DNA polymerase and a nucleotide analog that possesses the ability to base pair with at least two of the nucleotide bases adenine, guanine, cytosine and thymine, under conditions that allow for DNA polymerase extension and incorporation of the nucleotide analog to occur.

In certain embodiments, the step of amplifying the isolated double-stranded nucleic acid fragments employs a thermostable DNA polymerase. Optionally, the thermostable DNA polymerase is Taq, Vent®(exo-), NEBNext® or KAPA HiFi™.

Another aspect of the instant disclosure provides a method for detecting a single-stranded break hotspot in a genome, the method involving: obtaining a sample that includes genomic double-stranded nucleic acid of one or more organisms; contacting the sample with DNA polymerase I and a nucleotide analog that possesses the ability to base pair with at least two of the nucleotide bases adenine, guanine, cytosine and thymine, under conditions that allow for DNA polymerase I extension and incorporation of the nucleotide analog to occur; contacting the sample with a tagged nucleotide and natural deoxyribonucleotides under conditions that allow for DNA polymerase I extension and incorporation of the tagged nucleotide and natural deoxyribonucleotides to occur; fragmenting the double-stranded nucleic acid in the sample, thereby producing a population of double-stranded nucleic acid fragments; isolating double-stranded nucleic acid fragments that have incorporated the tagged nucleotide from the population of double-stranded nucleic acid fragments; ligating an exogenous oligonucleotide sequence to the double-stranded nucleic acid fragments; amplifying the isolated double-stranded nucleic acid fragments having the exogenous oligonucleotide sequence, thereby forming an amplified population of isolated double-stranded nucleic acid fragments; identifying the sequence of the amplified population of isolated double-stranded nucleic acid fragments; and within a number of sequences obtained from the amplified population of isolated double-stranded nucleic acid fragments, identifying in each sequence a series of three or more consecutive nucleotide positions that have at least two or more detectable nucleotide residues present at a level of at least 10% of all nucleotide residues detected at that position, at each of the three or more consecutive nucleotide positions, thereby identifying the presence and position of single-stranded breaks within a double stranded nucleic acid; and identifying at least two of the number of sequences as having the same position of single stranded break, thereby identifying the presence and position of a single-stranded break hotspot within a genomic double-stranded nucleic acid of an organism.

In one embodiment, the step of identifying at least two of the number of sequences as having the same position of single strand break involves comparing the presence and position of a first single-stranded break within a genomic double-stranded nucleic acid of an organism with the position of a second single-stranded break within a genomic double-stranded nucleic acid of an organism; and if the sites of the first and second single-stranded breaks are the same and occur at a prevalence that is significantly greater than chance, identifying the location of the first and second single-stranded break as a single-stranded break hotspot in the genome of the organism.

In certain embodiments, the one or more organisms include a bacteria, optionally the one or more organisms are bacteria, optionally bacterial cells in vitro and/or in culture.

In some embodiments, the one or more organisms include a eukaryote. Optionally, the one or more organisms are eukaryotic. Optionally, the eukaryote(s) are mammalian. Optionally, mammalian cells in vitro and/or in culture.

In one embodiment, the one or more organisms have been contacted with an agent, optionally a mutagenic agent, and the method is practiced to identify, e.g., mutational SSB hotspot(s).

In another embodiment, the one or more organisms have been contacted with a therapeutic agent, optionally a chemotherapeutic agent and/or an antibiotic. In such embodiments, the method of the disclosure may be practiced to identify a SSB hotspot in the organism(s), e.g., that have been induced by contact with the agent.

In an additional embodiment, the one or more organisms have been exposed to an altered environmental condition, optionally the one or more organisms have been subjected to an environmental condition such as low oxygen and/or anaerobic conditions, altered nutrients and/or drug exposure. In such embodiments, the method of the disclosure may be practiced to identify a SSB hotspot in the organism(s), e.g., that have been induced by exposure to the altered environmental condition.

A further aspect of the instant disclosure provides a method for detecting off-target Cas9 nicking activity involving: administering Cas9 to a mammalian cell; obtaining a double-stranded nucleic acid sample from the mammalian cell; contacting the sample with DNA polymerase I and a nucleotide analog that possesses the ability to base pair with at least two of the nucleotide bases adenine, guanine, cytosine and thymine, under conditions that allow for DNA polymerase I extension and incorporation of the nucleotide analog to occur; contacting the sample with a tagged nucleotide and natural deoxyribonucleotides under conditions that allow for DNA polymerase I extension and incorporation of the tagged nucleotide and natural deoxyribonucleotides to occur; fragmenting the double-stranded nucleic acid in the sample, thereby producing a population of double-stranded nucleic acid fragments; isolating double-stranded nucleic acid fragments that have incorporated the tagged nucleotide from the population of double-stranded nucleic acid fragments; ligating an exogenous oligonucleotide to the double-stranded nucleic acid fragments; amplifying the isolated double-stranded nucleic acid fragments having the exogenous oligonucleotide, thereby forming an amplified population of isolated double-stranded nucleic acid fragments; identifying the sequence of the amplified population of isolated double-stranded nucleic acid fragments; within a sequence obtained from the amplified population of isolated double-stranded nucleic acid fragments, identifying a series of three or more consecutive nucleotide positions that have at least two or more detectable nucleotide residues present at a level of at least 10% of all nucleotide residues detected at that position, at each of the three or more consecutive nucleotide positions, thereby identifying the presence and position of a single-stranded break within a double stranded nucleic acid; comparing the position of the single-stranded break with a predicted position of Cas9 activity in the mammalian cell, where if the position of the single-stranded break differs from the predicted position of Cas9 activity in the mammalian cells, thereby identifying the single-stranded break as a site of off-target Cas9 nicking activity, thereby detecting off-target Cas9 nicking activity in the mammalian cell.

In one embodiment, administering Cas9 to the mammalian cell is performed as a component of a CRISPR/Cas9 gene editing procedure, optionally where a CRISPR/Cas9 procedure single guide RNA (sgRNA) is assessed for its ability to direct off-target Cas9 nickase activity. In related embodiments, a number of sgRNAs are compared with one another using the instant method, in certain embodiments to identify a sgRNA that minimizes and/or eliminates off-target Cas9 nickase activity in a mammalian cell.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A degenerate nucleotide can have 2-fold degeneracy (i.e., it can be one of two nucleotides), 3-fold degeneracy (i.e., it can be one of three nucleotides), or 4-fold degeneracy (i.e., it can be one of four nucleotides. A or C or G or T).

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some of the base pairs are complementary. The bases that are not complementary are "mismatched." Complementarity may also be complete (i.e., 100%), if all the base pairs of the duplex region are complementary.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine) or nucleotide analogs. A nucleotide analog refers to a nucleotide having a modified purine or pyrimidine base or a modified ribose moiety. A nucleotide analog may be a naturally occurring nucleotide (e.g., inosine) or a non-naturally occurring nucleotide (e.g., dPTP, dKTP, etc.). Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos. Certain forms of nucleotide analog of the instant disclosure are capable of base pairing with more than one standard nucleotide, thereby producing a degeneracy of nucleotide base sequence following extension of a population of strands complementary to the nucleotide analog, e.g., as occurs during PCR amplification of a double-stranded nucleotide sequence.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) may be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm may be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs may be found on the GenBank website.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (So!exa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, er al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, an "antibiotic" refers to an agent used for elimination of bacteria, such as for treatment of infections therefrom. Exemplary antibiotics for use in the methods herein are those that eliminate gut bacteria, e.g., penicillin, streptomycin, ampicillin, neomycin, metronidazole, vancomycin, tazobactam, meropenem, or mixtures thereof, as well as anti-cancer antibiotics, which include, but are not limited to, anti-cancer antibiotics such as doxorubicin hydrochloride (adriamycin), idarubicin hydrochloride, daunorubicin hydrochloride, aclarubicin hydrochloride, epirubicin hydrochloride and pirarubicin hydrochloride, phleomycins such as phleomycin and peplomycin sulfate, mitomycins such as mitomycin C, actinomycins such as actinomycin D, zinostatin stimalamer and polypeptides such as neocarzinostatin.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

In FIG. 5A, two nick sites were generated in a plasmid, using the nicking restriction enzyme Nb.BsmI. Flaps were generated at the nick site using vent (exo-), and sequencing adapter (shown in lighter color at 5' ends) was single-stranded ligated to the 5' end of the flap using T4 RNA ligase. Efficiency was measured via qPCR by taking the fraction of adapters bound to total plasmid in the sample. Initial confirmation of results was performed via Sanger sequencing. FIG. 2B shows that the location of nick sites was identified with only 0.5-1.5% efficiency via qPCR, with efficiency varying dependent on adapter length. QPCR products were confirmed via gel electrophoresis on a 1% agarose gel. FIG. 2C shows that next-generation sequencing (NGS) results showed low specificity, as most reads did not map to the nick site.

FIG. 7A shows bar plots of base call frequencies along a nicked template for Taq polymerase reactions. FIG. 7B shows bar plots of base call frequencies along a nicked template for Kapa HiFi™ polymerase reactions. Taq polymerase and Kapa HiFi polymerase therefore showed distinct differences in the bias for the standard nucleotides in templates containing Ps and Ks. Oligonucleotides were annealed to form a SSB at various positions indicated by the black diamond and were designed such that the nick would begin at either an A, C, T or G. Nucleotide analogs that produced a degenerate site during complementary strand extension gave rise to a unique signal when library molecules were amplified by Taq and Kapa HiFi™ polymerases in the presence of nucleotide analogs. In particular, a decaying stretch of apparent heterozygosity (created by alternative base incorporation during polymerase-mediated extension of sequences annealing to a nucleotide analog (e.g., dPTP and/or dKTP)-containing sequence. (Such decay of apparent heterozygosity tends to occur across four, five, six or even more (e.g., ten or twelve, or more) oligonucleotide residues, and can be readily observed during sequencing, including next-generation sequencing reactions.)

FIG. 9A shows results for NickSeq libraries prepared without a streptavidin bead pulldown. FIG. 9B shows results for NickSeq libraries prepared with a streptavidin bead pulldown, where the instant "NickSeq" process exhibited two obvious peaks when performed upon the exemplary double-nicked plasmid of FIG. 8. The thick and thin vertical dashed lines identify the location of the single stranded break and the width of the peak as called by MACs2, respectively. The horizontal dashed line in FIG. 9A shows the 50% coverage level. Coverage was normalized to the max sequencing depth per sample.

FIG. 14A shows receiver operator characteristic (left) for identifying peaks in sequencing coverage at the location of nicks. The two dashed lines are thresholds at $1/10^{-5}$ and $1/10^{-3}$ from left to right, respectively. The false positive rate was defined as the number of peaks identified in regions that should have exhibited no nicks. The sequencing coverage plot for increasing amounts of background reads and hence a dilution of the unexpected base fraction (right) is also shown. The thick and thin vertical dashed lines identify the location of the single stranded break and the width of the peak as called by MACs2 respectively. Coverage was normalized to the max sequencing depth per sample. FIG. 14B shows the base fraction of the 5'-most base relative to the nick position plotted against the amount of noise added to the sequencing data.

FIG. 15A shows a schematic structural image of base pairing of the ribavirin base with either cytosine or thymine. FIG. 15B shows performance of dRTP, as compared with and as a possible replacement for dKTP, in the "NickSeq" process of the instant disclosure (displayed sequence is 5'-TGAGTCACTTG-3', SEQ ID NO: 5), when Taq DNA polymerase, Therminator DNA polymerase or *Sulfolobus* DNA polymerase IV were used.

FIG. 17A shows normalized base coverage results obtained for desthiobiotinylated dCTP (DTB-dCTP), as compared to use of biotinylated dUTP (B-dUTP). FIG. 17B shows normalized base coverage results obtained for desthiobiotinylated dATP (DTB-dATP), as compared to use of biotinylated dUTP (B-dUTP).

FIG. 19A shows a plasmid map for the plasmid used in testing for detection of activity of the nicking endonuclease Nb.BsmI upon the plasmid. The red arrowheads (two arrowheads, positioned at four- and eight-o-clock, respectively, in the plasmid image) represent the target sites, while purple arrowheads represent locations of off-target activity. FIG. 19B shows the results of such testing of detection of nicking endonuclease Nb.BsmI activity. Black dashed lines represent the target sites (corresponding to the two "NickSeq" peaks in the results) while purple and cyan lines represent reference and non-reference strand off-targets respectively. FIG. 19C shows a plasmid map for the plasmid employed for detection of Cas9 nickase cutting, with the on-target arrowhead positioned at approximately two-o-clock in the image, while the off-target site arrowhead is positioned at nearly six-o-clock in the image. FIG. 19D shows "NickSeq" signal results, which demonstrate NickSeq detection of both target and off-target sites of Cas9 guide RNA-mediated cutting in the plasmid of FIG. 19C.

FIG. 20A shows a circular plot of a bacterial genome, where one guide RNA targeted eight locations (red arrowheads) and another guide RNA targeted one location (purple arrowhead, positioned at 3-o-clock on the image). Circular plot represents normalized sequencing coverage with peaks identified by MACs2 colored in green and peaks containing the SSBs colored in red. FIG. 20B shows MACs2 peak p values, which exhibited prevalent false positives when sequence coverage alone was assessed. FIG. 20C shows normalized base coverage and one minus base call accuracy results, which demonstrated that the eight breaks caused by the first guide RNA could all be identified with single nucleotide resolution. FIG. 20D shows "NickSeq" results for the lone break caused by the second guide RNA, which was identified using the mutational signature unique to the "NickSeq" process of the instant disclosure.

DETAILED DESCRIPTION OF THE INVENTION

The present disclosure is directed, at least in part, to the discovery that single stranded breaks (SSBs—believed to be the most prevalent type of DNA damage) can be measured in DNA at single base pair resolution via implementation of a nick translation-type DNA polymerase I extension in the presence of one or more nucleotide analogs that are each capable of base pairing with at least two standard nucleotide bases (adenine, guanine, thymine and/or cytosine) at sufficiently high prevalence to allow for detection of such sites of nucleotide analog integration as degenerate sites when amplification and sequencing of such nick translated/nucleotide analog-exposed tracts of sequence is performed. The instant disclosure therefore provides for measurement of the exact location of SSB damage in DNA, e.g., genomic DNA.

Several enzymes are also known to work by causing a break in the DNA, such as those observed with Cas9 nickases and base editors. The ability to measure single-stranded breaks with locational precision, as is described herein, has application in studying off-target sites (e.g., genomic off-target sites) that harbor a DNA nick, as well as for understanding mutational biases across the genome, either that occur naturally or that might be induced by external agents and altered environmental conditions. Previously, the location of such damage has only been localized by pulldown assays, which have provided only poor resolution of the site of actual damage. Advantages of the instantly disclosed approaches include single base pair resolution and accurate quantification of the number of single-stranded break sites that occur within a genome.

Figure 1:
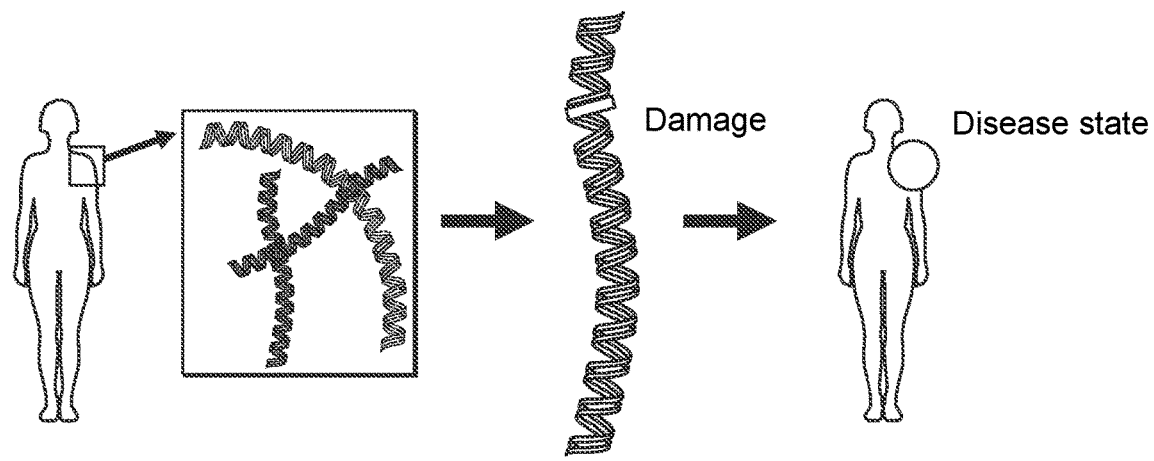
FIG. 1 shows an illustration of a person with a genetic disorder caused by DNA damage that has led to a disease state.

Understanding DNA damage is critical to understanding evolution and disease. As shown in FIG. 1, DNA damage is a critical component of evolution, as altering the genetic code can confer selective advantages. DNA damage, such as base pair substitutions, deletions, or additions, can also lead to disease states such as cancer, Huntington's disease, and many others. Single-stranded DNA breaks (SSBs or nicks) are believed to be the most common form of DNA damage in human cells, occurring at a rate of approximately tens of thousands of SSBs per cell per day.

Previously disclosed methods for identifying SSBs have been largely incapable of resolving the exact location of a nick, particularly when next-generation sequencing approaches have been employed. By example, while a Sanger sequencing chromatogram is capable of identifying DNA damage among large amounts of background undamaged DNA, to use such an approach, there is a need to perform Sanger sequencing upon entire genomes to obtain positional information. (See, e.g., Riedl, J., Ding, Y., Fleming, A., Burrows, C. Nature Communications 2015, which describes a method that removed damage, replaced it with a labeled nucleotide, and Sanger sequenced the full genome.) Alternatively, methods described in the art for identifying a single-stranded nick have involved finding a region of damage without detecting specific hotspots. Larger regions of damage are therefore identified by such methods: while the throughput provided by such methods of identifying regions has been an advantage, a critical weakness of such approaches has been the difficulty of quality control of such high-throughput data, as well as the fact that no exact matches for damage sites can be identified via such approaches.

The compositions and methods of the instant disclosure improve both the sensitivity and specificity of nick identification. Advantageously, the instantly described approaches identify the exact location of damage rather than a region; allow for more specific conclusions to be drawn about hotspots; and provide that additional advantage that locating SSBs can be performed modularly for other types of DNA damage (See Helleday, T., Eshtad, S. & Nik-Zainal, S. Nature Reviews Genetics 2014).

As noted above, single strand breaks occur at the rate of approximately 10,000 per cell per day. Without wishing to be bound by theory, the most common causes of SSBs include oxidative stress and erroneous and/or abortive behavior of enzymes such as DNA topoisomerase I. In an exemplary deleterious scenario, the presence of a nick in genomic DNA can lead to the collapse of replication forks, especially in scenarios where there is an increase in the number of single strand breaks (Caldecott, K W. Single strand break repair and genetic disease. Nat Rev Genetics. (9) 2008).

Cas9 nickases and base editors also rely upon creating a single stranded break as part of their function (FA Ran, et al. Double Nicking by RNA-Guided CRISPR Cas9 for Enhanced Genome Editing Specificity. Cell. (154) 2013). In an exemplary scenario, two sgRNAs can be used at a distance of an n base pair offset between a first sgRNA on one strand and a second sgRNA located on the opposite strand, with each location accessed and nicked by Cas9. Cas9 nickases and base editors rely upon creating a single stranded break as part of their function. Prior to the instant disclosure, there has been no efficient way to measure whether these types of enzymes are targeting the desired locations (i.e., those intended to be directed by an sgRNA design) (Gaudelli, N M, et al. Programmable base editting of AT to GC in genomic DNA without DNA cleaveage. Nat. (551) 2017). A significant advantage of the instant disclosure is therefore the provision of a method for identifying off-target Cas9 activity, e.g., during CRISPR/Cas9 gene editing procedures.

While to date there has been no efficient strategy for identification of the exact position of single stranded breaks, methods to identify double stranded breaks have been extensively described in the art and include: guide seq; HTGTS; BLESS; Circle seq; Digenome seq; and an SSB-Seq approach set forth in Baranello, L, et al. (DNA break mapping reaveals topoisomerase II activity genome-wide. IJ of Mol Sci. (15) 2014). The Baranello approach is exemplary of art-recognized approaches for detecting single-stranded breaks: the process involves antibody pulldowns in combination with nick translation but does not provide the instantly disclosed methods: in Baranello, single-stranded breaks occur; DNA Pol I then extends from the break with dU-DIG and dNTPs, where dU-DIGs are subject to antibody pulldown (sonication anti-DIG). After pulldown, sequencing has been performed to detect locations (roughly) of SSBs.

Certain advantages of the instantly disclosed approaches for SSB detection include the single base pair resolution for damage that the instant methods provide (due to the decay of signature across a number of bases—i.e., 10-13 bases of signature/degradation is typical when using the instant approaches). Because of their precision, the instant approaches can also detect single-stranded nicks (noting that Cas9 nicks tend to be spaced at a distance of at least 20 bp.

The instant provision of improved SSB detection is of diagnostic and therapeutic importance, at least because SSBs are so common and have been described as disease-associated. In particular, γ-rays are effectively omnipresent, as is nucleotide excision repair within cells. Detection of (unrepaired) SSBs is useful for disease detection, and is also useful for detection of oxidative stress, mutagenic drug impact, chemotherapeutic impact, antibiotic impact (e.g., allowing for measuring antibiotic-induced damage in targeted bacteria, as well as other antibiotic impacts that might enhance or prevent development of bacterial resistance (contemplated as relevant to identifying second lines of antibiotic treatment, among other applications), etc. In certain embodiments of such applications, the assay can be performed upon DNA extracted from treated cells. In other embodiments, it is contemplated that a mutational landscape (e.g., responsive to a drug, antibiotic, etc.) for SSBs within a cell or organism can be assessed using the methods of the instant disclosure.

Detection of SSBs in promoters is also contemplated, e.g., as aiding identification of disease impact. It is further contemplated that the instant methods can aid in screening for agents that are capable of preventing SSB damage, particularly where SSB hotspots have been identified.

The ability to precisely measure off-target effects, particularly with DNA editing technologies such as CRISPR/Cas9, are an additional advantage provided by the compositions and methods of the instant disclosure.

The instantly exemplified methods have been approximated to possess sufficient sensitivity to be capable of detecting one nick per cell per one thousand cells.

Presented herein is a new DNA SSB mapping approach, called "NickSeq", to sequence specific locations of breaks with single nucleotide resolution. It has been demonstrated herein that sites of SSBs were enriched 1000-fold in windows of 500 base pair regions and that individual locations of the breaks could be detected to single nucleotide resolution due to a unique mutational signature at the site of damage.

DNA damage is a process that happens continuously throughout the lifetime of a cell due to endogenous (DNA hydrolysis, oxidative stress, polymerase stalling) and exogenous (UV radiation, IR, chemotherapies) sources and can result in the formation of double stranded breaks (DSBs), SSBs, DNA lesions, etc. (Ciccia 2010). In addition, the repair mechanisms responsible for correcting these types of damage, base excision repair (BER) and nucleotide excision repair (NER), both proceed through a SSB intermediate. SSBs are the most abundant type of damage and occur at an estimated frequency of about 10,000 per cell per day (Caldecott 2008, Bradley 1979, Takashima 2002). Although the formation of SSBs are common through both damage and repair, it is unknown precisely how many and where these breaks occur in cells. Key mutations in SSB repair machinery have been implicated in progressive neurological dysfunction such as spinocerebellar ataxia with axonal neuropathy 1 (SCAN1) and ataxia oculomotor apraxia 1 (AOA1) (Date 2001, Moreira 2001). Furthermore, specific accumulation of DNA SSBs have been associated with heart failure in mice due to an increase in inflammatory gene expression (Higo 2017). Lastly, DNA SSBs have been observed to accumulate in telomeric regions and be correlated to an increase in telomere shortening rate through an unknown mechanism (Zglinicki 2002).

Despite the correlation between SSB and disease state, it is not well understood how the amount and location of damage are related to the resultant phenotypic response. The comet assay is the gold standard for measuring the extent of DNA damage and can be used to measure both DSB and SSB. However, this approach provides a relative measure of damage to a control and hence it is difficult to precisely quantify the number of breaks, and the locations at which they occur. Although there are many alternative approaches to identify where DSBs occur in DNA (Yan 2017, Crosetto 2013, Lensing 2016, Tsai 2015, Hu 2016, Tsai 2017), there has, to date, been no reported method by which to determine the exact location of SSBs. Single base resolution of damage, as provided herein, can provide mechanistic insight into observed mutational patterns and diseased phenotypes. For example, hotspot mutations in promoters of certain cancer cell lines were associated with NER by sequencing of unique excised fragments from the repair pathway (Poulos 2015, Melton 2015, Perera 2016}. In addition, it is well known that DNA damage can be biased to specific sequence motifs, but the patterns of damage from SSBs have not been measured (Gale 1987). However, there are distinct correlations between locations of damage in DNA and the mutational distributions that arise in the genome (Brash 1982).

Moreover, with the advent of novel technologies for DNA manipulation by single strand nicking for genome editing, there is a greater need to robustly identify the location of either on-target or off-target nick generation. An indirect approach that interrogates the modification of cytosine to uracil offers some insight into the non-specificity of cas9 base editors (Kim D 2017). However, this method is specific to only identifying and creating a DSB break at uracil locations. Without wishing to be bound by theory, a SSB has inherent differences and challenges that makes mapping the damage profile more difficult compared to DSBs. It is enzymatically challenging to both ligate an adapter at the site of a nick and also determine which strand the damage occurred on since SSBs are strand specific. Correctly determining which strand the damage occurs on can have implications for the biases that exist for damage as well as the efficiency of repair at these locations (Mellon 1987).

The instant disclosure has shown what appears to be the first measurement of SSBs with single nucleotide resolution. The methods of the instant disclosure build upon previous work that has utilized nick translation (Rigby 1977) to incorporate modified nucleotides at the SSBs (Baranello 2014). It has been demonstrated herein that the combination of a unique identifier and enrichment of SSB sites has allowed for the identification of damaged sites with nucleotide resolution. This type of measurement can enable insight into both the amount of damage a cell can handle as well as any damage biases.

In particular, the instant disclosure has demonstrated that the exact location of SSBs can be identified through a unique mutational signature arising from a set of universal bases at the site of damage. Significantly, the instantly disclosed techniques provide the capability to measure the SSB damage profiles arising, e.g., due to the exposure of cells to both endogenous and exogenous stimuli such as UV light, therapeutic compounds, reactive oxygen species, and enzymatic activity. Further, the single base resolved damage profiles can offer insight into the correlations of SSBs with neurological disorders such as ataxia. NickSeq as disclosed herein can also likely resolve damage biases arising due to the DNA structure and offer absolute quantification on the number of SSBs through UMI analysis.

The instant approach towards detection of SSBs therefore leverages the enormous progress made in developing variant calling tools, since the instant disclosure converts the signature of a break to a list of consecutive variants (McKenna 2010, Li 2014). This method generates consecutive single nucleotide variants (SNVs) as opposed to the traditional role of variant callers that look for randomly dispersed variants across the genome. The net result is that the instantly disclosed NickSeq damage profile is unique and can be distinguished from sequencing noise much more readily than standard SNVs. A key aspect that NickSeq provides is therefore also high resolution stranded information towards the site of SSB damage, which no other method has readily provided. This characteristic can enable a more quantitative understanding of biology, such as the observation that specific accumulation of SSBs is correlated to an increase in shortening rate of telomeres resulting in cell senescence (Zglinicki 2002). Without wishing to be bound by theory, a key question in SSB biology that remains to be answered is how the distribution of SSBs in terms of amount and stranded information contributes to telomere shortening and aging in general (Nassour 2016).

Importantly, the detection of single stranded breaks also has critical application to genome engineering. The recent surge in using nickases to increase guide RNA specificity and base editors to make specific mutations at targeted locations across the genome utilizes the formation of a SSB in the editing mechanism. The creation of this break is the signal for repair machinery to edit the genome by either homologous recombination or through base excision repair. To date, there exists no method to globally measure the frequency at which the guide RNA mistargets the desired location and creates a SSB in unknown locations. The instant approach can therefore be used to screen and filter for guides that have minimal crosstalk with locations outside the targeted genomic sequence. The process of the instant disclosure is therefore a promising platform technology to quantitatively interrogate SSB damage across the genome and can elucidate mechanisms or thresholds required before disease phenotypes arise.

Nick Translation Reactions

Nick translation (also referred to as head translation), was developed in 1977 by Rigby and Paul Berg (Rigby et al. J. Mol. Biol. 113 (1): 237-51), and is a tagging technique in molecular biology in which DNA Polymerase I is used to replace some of the nucleotides of a DNA sequence with their labeled analogues, creating a tagged DNA sequence which can be used as a probe in fluorescent in situ hybridization (FISH) or blotting techniques. It can also be used for radiolabeling (Mathew C G (1985). Methods Mol. Biol. 2: 257-61). The process is called nick translation because the DNA to be processed is treated with DNAase to produce single-stranded "nicks". This is followed by replacement in nicked sites by DNA polymerase I, which elongates the 3' hydroxyl terminus, removing nucleotides by 5'-3' exonuclease activity, replacing them with dNTPs. In exemplary use of nick translation, to radioactively label a DNA fragment for use as a probe in blotting procedures, one of the incorporated nucleotides provided in the reaction is radiolabeled in the alpha phosphate position. Similarly, a fluorophore can be attached instead for fluorescent labelling, or an antigen for immunodetection. When DNA polymerase I eventually detaches from the DNA, it leaves another nick in the phosphate backbone. The nick has "translated" some distance depending on the processivity of the polymerase. This nick could be sealed by DNA ligase, or its 3' hydroxyl group could serve as the template for further DNA polymerase I activity. Proprietary enzyme mixes are available commercially to perform all steps in the procedure in a single incubation.

Nick translation has been identified as capable of causing double-stranded DNA breaks, if DNA polymerase I encounters another nick on the opposite strand, resulting in two shorter fragments.

Nucleotide Analogs dPTP

2'-Deoxy-P-nucleoside-5'-Triphosphate (dPTP) has the following structure:

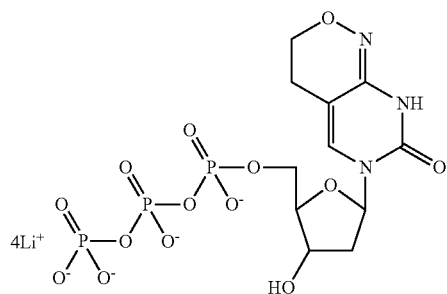 [SMILES: O=C1NC2=NOCCC2=CN1C1CC(O)C(COP(=O)([O-])OP(=O)([O-])OP(=O)([O-])[O-])O1]

Figure 4:
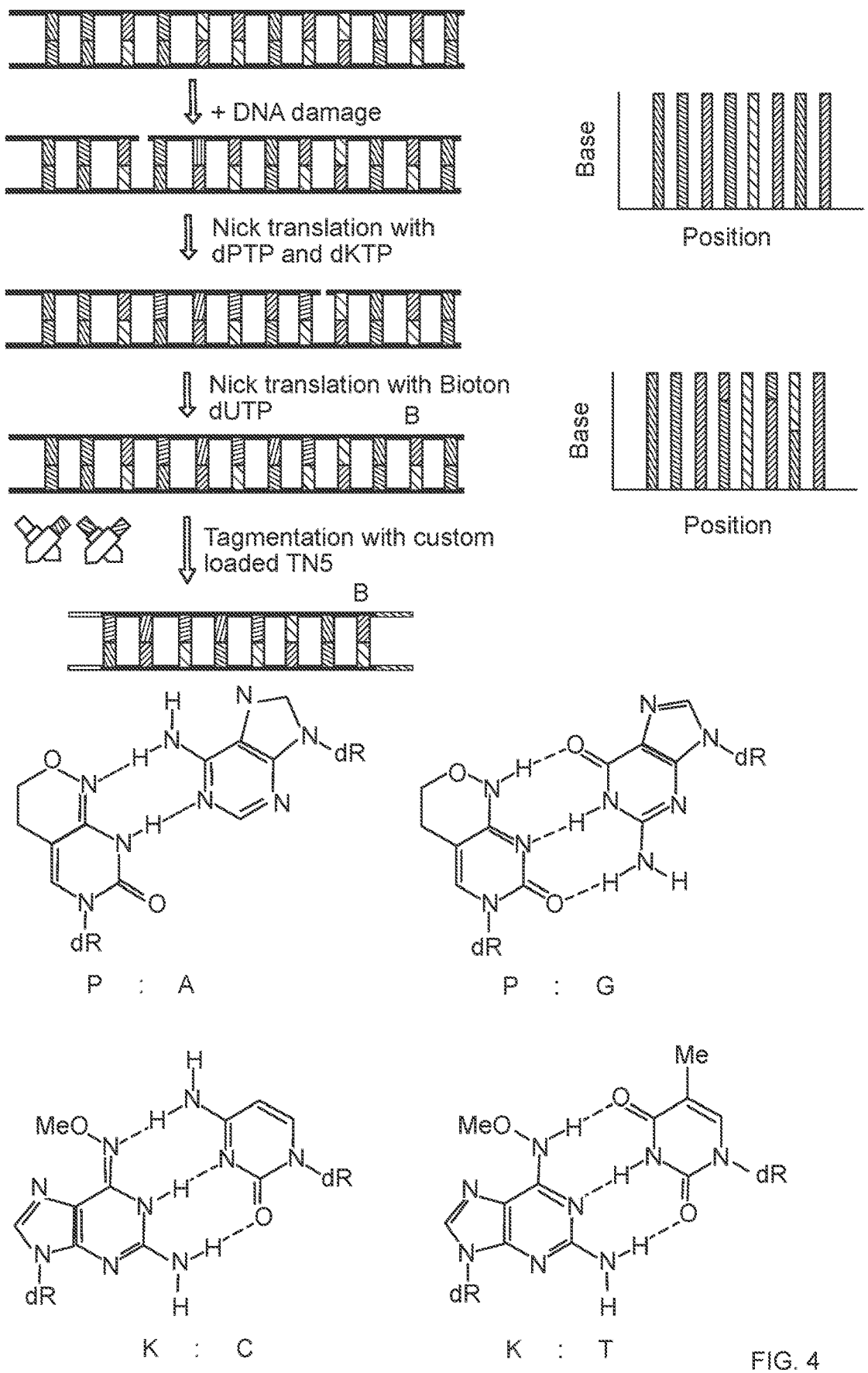
FIG. 4 shows that the instant "NickSeq" method can be used to identify the location of potential off-target enzymatic nicking and to identify biased single stranded break damage. In particular, the process allows for identifying and enriching for locations of single-stranded breaks in DNA. dPTP and dKTP can each base pair with two of the canonical bases. P base pairs with A and G whereas K base pairs with T:C at ratios of 60:40 and 85:15 respectively (Hill 1998). A schematic of converting a SSB to a unique mutational signature is also shown, in which nick extension beginning at the damaged backbone with only dPTP and dKTP resulted in non-natural bases being incorporated at the site of the SSB. Followed by extension with standard dNTPs and biotin-11-dUTP enabled the enrichment of molecules containing dPTP and dKTP after library construction. UMI incorporation during the tagmentation step allowed for absolute quantification of the number of SSBs in the sequencing library. The bottom panel shows representative sequencing base calls for a molecule with Ps and Ks in the template (bottom bars) compared to the base calls without the non-natural nucleotides (top bars). Due to the universal bases in the template, a unique signature of mutation was seen at the site of the break when the molecule was amplified by PCR.

As presented in FIG. 4, dPTP, when introduced into an oligonucleotide context as a "P" nucleotide residue, tends to base pair with purine residues, at an approximately 60% rate with adenine ("A") and at about a 40% rate with guanine ("G").

dKTP $N^6$-Methoxy-2,6-diaminopurine-2'-deoxyriboside-5'-O-triphosphate (dKTP) has the following structure:

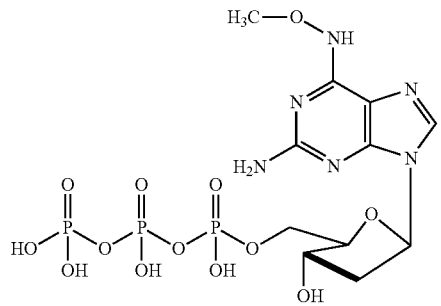

As presented in FIG. 4, dKTP, when introduced into an oligonucleotide context as a "K" nucleotide residue, tends to base pair with pyrimidine residues, at an approximately 85% rate with thymine ("T") and at about a 15% rate with cytosine ("C").

RTP

1-β-D-Ribofuranosyl-1,2,4-triazole-3-carboxamide-5'-O-triphosphate (Ribavirin-5'-O-triphosphate; RTP), sodium salt, has the following structure:

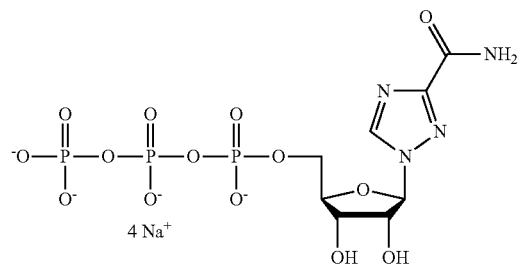

1-β-D-deoxyribofuranosyl-1,2,4-triazole-3-carboxamide-5'-O-triphosphate (deoxy-Ribavirin-5'-O-triphosphate; dRTP), sodium salt, correspondingly has the following structure:

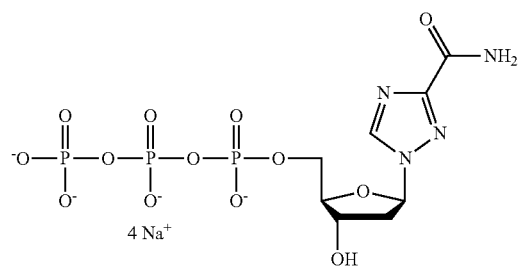

Other Universal and Degenerate Nucleotide Analogs

Universal bases exhibit the ability to replace any of the four normal bases (for DNA, adenine, guanine, thymine and cytosine) without significantly affecting either melting behavior of duplexes or the normal activities of the modified oligonucleotide. Degenerate bases (degeneracy-producing nucleotide analogs) effectively code as two or more but not all of the normal bases. Traditional use of universal and degenerate bases has been in the context of oligonucleotide primer sequence synthesis (e.g., for PCR amplification and/or sequencing), where primer multiplicity can be eliminated via use of universal bases and can be reduced via use of degenerate bases.

Structures of exemplary universal bases include:

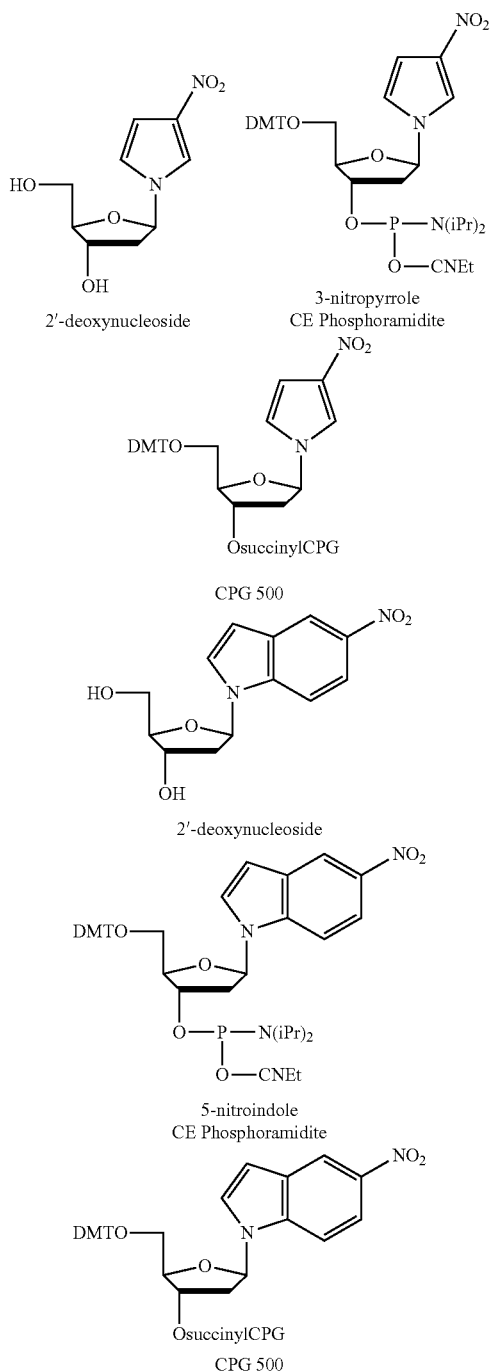

3-nitropyrrole-CE phosphoramidite which was designed by researchers at Purdue University and the University of Michigan as a universal base (Nichols et al. Nature, 369: 492-493; Bergstrom et al. J. Am. Chem. Soc., 117: 1201-1209). The strategy behind the development of 3-nitropyrrole was elegantly simple. Duplexes containing 3-nitropyrrole were stabilized by stacking interactions rather than by hydrogen bonding, thereby removing any bias for an individual complementary base. Nevertheless, duplexes containing 3-nitropyrrole at one or more positions were significantly destabilized relative to the fully complementary duplex. A subsequent report (Loakes and Brown. Nucleic Acids Res., 22: 4039-4043) described the preparation of nitroindole-CE phosphoramidites and their use as universal bases. The researchers compared 4-, 5- and 6-nitroindole with 3-nitropyrrole as universal bases. Like 3-nitropyrrole, all three nitroindole isomers acted indiscriminately towards the four natural bases. Furthermore, based on duplex melting experiments, 5-nitro-indole was determined to be the most effective of the nitroindole isomers and to be superior to 3-nitropyrrole. The order of duplex stability was found to be 5-nitroindole>4-nitroindole>6-nitroindole>3-nitropyrrole.

Degeneracy-Producing Nucleotide Analogs P and K

As described above, dPTP and dKTP can be employed as nucleotide analogs that produce degenerate sequences when complementary strands are extended, e.g., during amplification. Indeed, dPTP and dKTP have been exemplified herein as particularly useful in the context of the instant disclosure. While some primer/template systems may be unable to tolerate the level of destabilization caused by these nucleotide analogs, the instant disclosure employs this destabilization to the advantage of detecting single-stranded break locations with precision.

Melting Behavior

The effect of substituting sites in primers with universal bases can be simply assessed using thermal dissociation experiments. As examples, it was found (Nichols et al. Nature, 369: 492-493; Loakes and Brown. Nucleic Acids Res., 22: 4039-4043) that substitution with 3-nitropyrrole and 5-nitroindole towards the termini of oligonucleotides was less destabilizing than substitution towards the center. This may confirm that the universal bases stabilize the duplex by acting as intercalators. Also, oligonucleotides were destabilized less if the universal bases were grouped together rather than dispersed through the oligonucleotide. With multiple insertions, 5-nitroindole was shown to be the least destabilizing of the universal bases. Indeed, six insertions of 5-nitroindole into an oligonucleotide was found (Loakes and Brown. Nucleic Acids Res., 22: 4039-4043) to be more stable than three insertions of 3-nitropyrrole based on stacking enthalpy measurements. Thermal stability studies have been important in validating the usefulness of bases as universal bases. However, performance of any purported universal or degenerate base-effecting nucleotide (nucleotide analog that produces degenerate sequence) in the real world of oligonucleotides for use in sequencing and PCR primers is also essential to evaluate.

Universal Bases Previously Used in Primers: 3-Nitropyrrole in Sequencing and PCR The behavior of 3-nitropyrrole in experiments using a specific primer/target system was initially reported (Nichols et al. Nature, 369: 492-493). In dideoxy sequencing experiments, oligonucleotides containing 3-nitropyrrole substitutions were compared to the complementary sequence and to sequences prepared with A, C, G, T mix (N) and 2'-deoxyInosine (dI) which represent the most common substitution strategies for universal base inclusion during primer synthesis. The sequence containing 3-nitropyrrole at the third position of four codons gave an unambiguous sequencing ladder. In contrast, the sequencing ladder obtained from the identical sequence containing dI was only partially readable, while that obtained using N (a 256 fold degenerate mixture of primers) was unreadable. Acceptable sequencing ladders were also obtained when one, two and even three codons adjacent to the 3'-terminus were completely replaced by 3-nitropyrrole. It was assumed that the 2 correct bases left at the 3'-terminus in these experiments were insufficient to maintain a normal duplex at 37° and so the 3-nitropyrrole bases must have contributed to correct duplex formation. Interestingly, an oligonucleotide containing 3-nitropyrrole at the 3'-terminus gave a readable sequencing ladder, whereas a mismatch at the 3'-terminus did not. This result indicated that 3-nitropyrrole was an effective substrate for the polymerase enzyme rather than simply blocking chain extension. The performance of PCR primers containing 3-nitropyrrole was thus studied briefly and the results showed promise for this universal base.

Initial results in sequencing experiments indicated that 3-nitropyrrole seemed to be performing very well. However, PCR experiments using primers with several insertions at the third position of several codons were problematical. Without wishing to be bound by theory, it was postulated that such PCR problems of 3-nitropyrrole occurred when the melting temperature of a duplex containing 3-nitropyrrole residues fell too low.

Universal Bases Previously Used in Primers: 5-Nitroindole in Sequencing and PCR

5-Nitroindole, due to its better stabilization properties, was advanced as possibly yielding improved performance relative to 3-nitropyrrole in certain difficult situations (Loakes and Brown. Nucleic Acids Res., 22: 4039-4043). A further publication (Loakes et al. Nucleic Acids Res., 23: 2361-2366) from Dan Brown's group at the Medical Research Council in Cambridge, England described a series of experiments that involved a stringent primer/template system used to evaluate the ability of duplexes containing universal bases 3-nitropyrrole and 5-nitroindole to prime DNA synthesis in both PCR and sequencing environments. In the system described, sequencing experiments were less spectacular than previously described (Nichols et al. Nature, 369: 492-493; Bergstrom et al. J. Am. Chem. Soc., 117: 1201-1209). Only primers containing one or two substitutions at codon third positions gave readable ladders, while those containing four to six substitutions failed to prime. Primers modified with up to four contiguous substitutions of 5-nitroindole led to readable ladders but only two 3-nitropyrrole substitutions were tolerated. For the template used, three contiguous substitutions of universal bases, two bases from the 3'-terminus of the primer, did not give readable ladders. Also in contrast to the previous work with 3-nitropyrrole, a primer with 5-nitroindole at the 3'-terminus did not give rise to a sequencing ladder, indicating that variations can occur among primers and templates.

Using substituted PCR primers, it was found that up to three contiguous 3-nitropyrrole substitutions and up to four 5-nitroindole substitutions were tolerated, as long as the substitutions were not adjacent to the 3'-terminus. Further substitution would likely be acceptable for PCR primers if the annealing temperature of the PCR experiment was lowered to accommodate the lower melting temperature of the duplex. Using primers containing substitutions at codon third positions, only two substitutions were tolerated for normal amplification. When four or six codon third positions were substituted by 5-nitroindole, a PCR product could be observed but in low yield. In this same system, a sequence containing six dI substitutions was an effective PCR primer.

Some aspects of the use of universal bases in sequencing and PCR experiments have therefore been clarified. The original report covering 3-nitropyrrole generated dramatic results which served to indicate the promise of this approach. The subsequent report about 5-nitroindole which offered at least equivalent results with less duplex destabilization, served to accentuate this interest. However, such promise did not translate into successful experiments in a wide variety of primers and templates, and certain aspects of the instant disclosure provide use of "universal" and/or degenerate (including non-natural universal and/or degenerate) base-producing nucleotide analogs during nick translation-type extension reactions, rather than the more traditional and better characterized use of such nucleotides within synthetic primer sequences. Accordingly, any number of the various "universal" and/or degeneracy-producing nucleotide analogs presented herein are expressly contemplated for assessment and use within the instant methods, with the expectation that optimization of universal and/or degeneracy-producing nucleotide analog use for the instant methods can be readily performed across a range of such universal and/or degeneracy-producing nucleotide analogs.

To summarize regarding past use of universal base nucleotides in the art, and without wishing to be bound by theory, the above-described primer-directed "universal" base experiments revealed that there appears to be no "universal" (i.e., universally applicable) universal base, at least as yet. Differing circumstances currently can dictate the use of 3-nitropyrrole, 5-nitroindole and/or dI or other universal base as a universal base. The degeneracy-producing nucleotide analogs P and K, described above and exemplified herein, are clearly useful for implementation of the methods of the instant disclosure, particularly in combination with one another.

The results described in the preceeding sections indicate that the search for the perfect universal base is not over. 3-Nitropyrrole and 5-nitroindole represent significant additions to the group of universal bases, though it has been noted that their destabilizing effect on duplexes has made them suitable for use in PCR primers with only a few substitution sites (however, this is likely to be less of an issue for employment of such degeneracy-producing nucleotide analogs in the methods of the instant disclosure). For primer design, dI has functioned relatively well in its role as a universal base (see, e.g., Haller et al. "Massively parallel single-nucleotide mutagenesis using reversibly terminated inosine." Nature Methods 13: 923-24) but its hybridization properties are not ideal and, when incorporated into PCR primers, it has been reported to code primarily as G (Lin and Brown. Nucleic Acids Res., 20: 5149-5152), a feature which has reduced dI's utility for certain methods of the instant disclosure, as use of dI has tended to result in G-rich tracts, as opposed to the readily distinguishable signal that the combination of dPTP and dKTP nucleotides was observed to yield in the instantly disclosed methods, as exemplified herein. Indeed, the modified bases shown below and in FIG. 4, designated P and K, have shown considerable promise as degeneracy-producing nucleotide analogs. The pyrimidine derivative P, when introduced into oligonucleotides, base pairs with either A or G (Lin and Brown. Nucleic Acids Res., 17: 10383), while the purine derivative K base pairs with either C or T (Brown and Lin. Carbohydrate Research, 216: 129-139). This is made possible by the ability of P and K to form both amino and imino tautomers, as shown in below and in FIG. 4. Oligonucleotides containing one or more P substitutions were found (Lin and Brown. Nucleic Acids Res., 20: 5149-5152) to form duplexes of stability equivalent to the parent sequence and exhibited sharp transitions on melting. Substitution with one or more K residues led to duplexes of reduced but still effective stability. A CE phosphoramidite of P which is equivalent to a C/T mix and of K which is equivalent to an A/G mix, is commercially available. The structures of the CE phosphoramidites are shown below. A P/K mix to be equivalent to an N (A/C/G/T mix) has also been offered commercially, and has been effectively used in the exemplified methods of the instant disclosure.

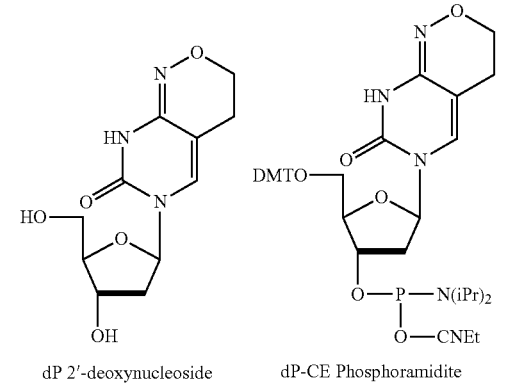

dP 2'-deoxynucleoside    dP-CE Phosphoramidite

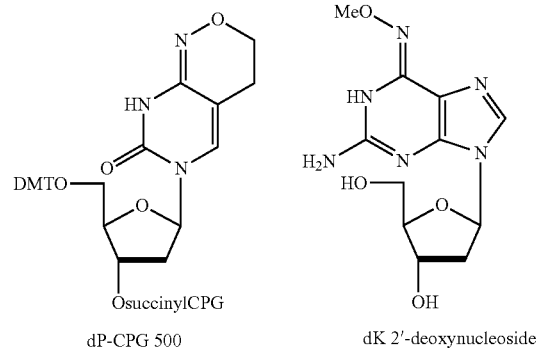

dP-CPG 500    dK 2'-deoxynucleoside

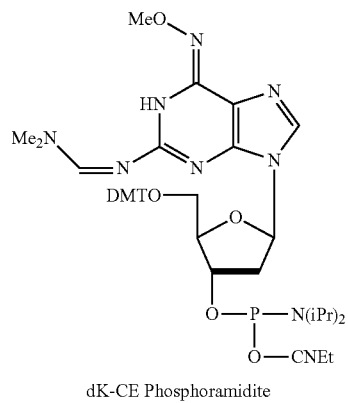

dK-CE Phosphoramidite

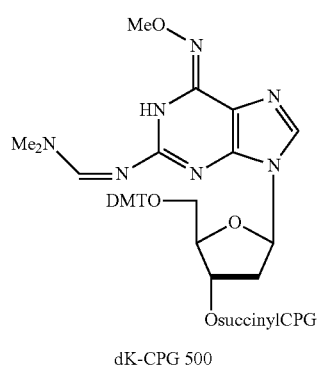

dK-CPG 500

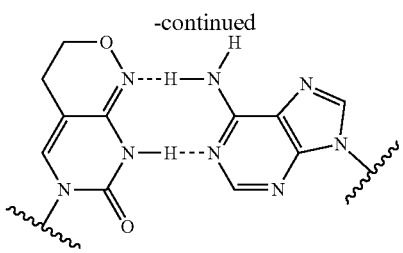

P-imino A

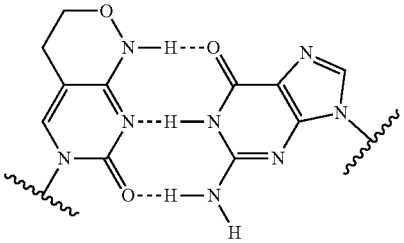

P-amino G

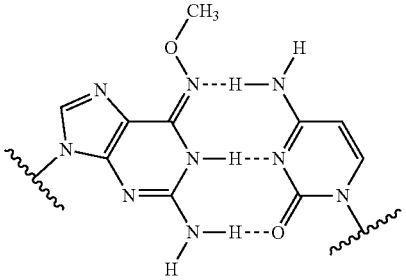

K-imino C

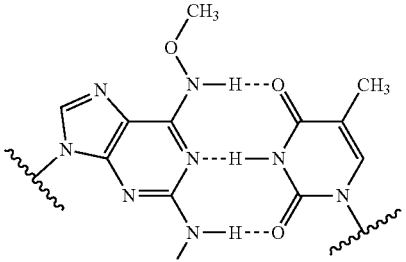

K-amino T

Hydrophobic nucleobases 3-methyl isocarbostyril (MICS), 5-methyl isocarbostyril (5MICS), and 3-methyl 7-propynyl isocarbostyril (PIM) have also been described as universal bases (Berger et al. Nucleic Acids Research 28: 2911-14):

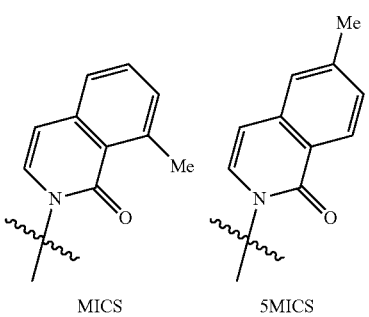

MICS    5MICS

-continued

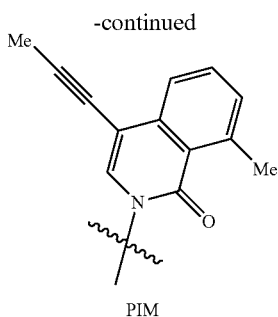

PIM

MICS and 5MICS have been described as base pairing more stably with dA and dC, as compared to dT and dG, while PIM has been described as base pairing slightly more stably with dA and dT, as compared with dC and dG (Berger et al. Nucleic Acids Research 28: 2911-14).

DNA Fragmentation

DNA fragmentation is the breaking of DNA molecules into smaller pieces. Fragmentation of DNA is an early step in next generation sequencing workflows, and a number of methods of DNA fragmentation are known in the art and specifically include:

(1) Enzyme-based treatments that fragment DNA by the simultaneous cleavage of both strands, or by generation of nicks on each strand of dsDNA to produce dsDNA breaks.

(2) Acoustic shearing using short wavelength acoustic energy that focuses transmission of high-frequency acoustic energy on the DNA sample, which can be performed isothermally. The transducer tends to be bowl shaped so that waves converge at the target of interest.

(3) Sonication using specialized sonicators that subjects DNA to longer wavelength, unfocused acoustic energy, and requires cooling periods between sonication bursts.

(4) DNA can also be sheared by the use of centrifugal force to move DNA through a hole of a specific size. The rate of centrifugation determines the degree of DNA fragmentation.

(5) Point-sink shearing, a type of hydrodynamic shearing, uses a syringe pump to create hydrodymanic shear forces by moving DNA through a tube with a tight constriction, such that the DNA breaks, with the size of the constriction and the flow rate of the liquid determining the DNA fragment size.

(6) Needle shearing, in which shearing forces are created by passing DNA through a small gauge needle.

(7) Nebulization, which uses compressed air to force DNA through a small hole in a nebulizer unit, and the fragmented, aerosolized DNA is collected. DNA fragment size is determined by the pressure used.

Exemplary average fragment sizes achieved for fragmented dsDNAs of the instant disclosure tend to be in the range of 20-4000 base pair fragments, with fragment populations having average fragment lengths grouped within various different subranges (e.g., 400-2000 base pairs in length, 300-800 base pairs in length, etc.) of this broader window contemplated as useful for performance of the instantly disclosed methods.

Oligonucleotide Adapter Sequences

A number of adapter and/or bar code oligonucleotide sequences have been described in the art. Adapter sequences that can be end-ligated to DNA fragments of the instant disclosure, e.g., to allow for amplification of isolated dsDNA fragments via use of universal PCR primers include, e.g., those previously described in U.S. Pat. No. 6,287,825 and U.S. Patent Publication No. 2017/0283869, among others. In the instant Examples, Nextera™ tagmentation sequences were end-ligated to dsDNA fragments, as previously described, e.g., in EP2635679, as well as WO 2016/189331.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

The tagmentation method can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

In standard sample preparation methods, each template contains an adaptor at either end of the insert and often a number of steps are required to both modify the DNA or RNA and to purify the desired products of the modification reactions. These steps can be performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence.

Transposases as described herein can be used in a sequencing procedure, such as an in vitro transposition technique. Briefly, in vitro transposition can be initiated by contacting a transposome complex and a target DNA. Exemplary transposition procedures and systems that can be readily adapted for use with the transposases of the present disclosure are described, for example, in WO 10/048605; US 2012/0301925; US 2013/0143774, each of which is incorporated herein by reference in its entirety.

CRISPR/Cas9 Gene Editing

CRISPR-Cas system activity, such as CRISPR-Cas system design may involve target disruption, such as target mutation, such as leading to gene knockout. CRISPR-Cas system activity, such as CRISPR-Cas system design may involve replacement of particular target sites, such as leading to target correction. CISPR-Cas system system design may involve removal of particular target sites, such as leading to target deletion. CRISPR-Cas system activity may involve modulation of target site functionality, such as target site activity or accessibility, leading for instance to (transcriptional and/or epigenetic) gene or genomic region activation or gene or genomic region silencing.

The CRISPR methods provided herein are exemplified for Cas9, a type II nuclease that requires a tracrRNA. Orthologs of Cas9 have been identified in different bacterial species as described previously (e.g. WO2014093712). Further type II nucleases with similar properties can be identified using methods described in the art (Shmakov et al. 2015, 60:385-397; Abudayeh et al. 2016, Science, 5; 353(6299)).

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819, 803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836, 080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915, 251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010, 879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, Jun. 17, 2015, PROTECTED GUIDE RNAS (PGRNAS); U.S. application 62/091,455, filed, Dec. 12, 2014, PROTECTED GUIDE RNAS (PGRNAS); U.S. application 62/096,708, Dec. 24, 2014, PROTECTED GUIDE RNAS (PGRNAS); U.S. applications 62/091,462, Dec. 12, 2014, 62/096,324, Dec. 23, 2014, 62/180,681, Jun. 17, 2015, and 62/237,496, Oct. 5, 2015, DEAD GUIDES FOR CRISPR TRANSCRIPTION FACTORS; U.S. application 62/091,456, Dec. 12, 2014 and 62/180,692, Jun. 17, 2015, ESCORTED AND FUNCTIONALIZED GUIDES FOR CRISPR-CAS SYSTEMS; U.S. application 62/091,461, Dec. 12, 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, Dec. 19, 2014, UNBIASED IDENTIFICATION OF DOUBLE-STRAND BREAKS AND GENOMIC REARRANGE- MENT BY GENOME-WISE INSERT CAPTURE SEQUENCING; U.S. application 62/096,761, Dec. 24, 2014, ENGINEERING OF SYSTEMS, METHODS AND OPTIMIZED ENZYME AND GUIDE SCAFFOLDS FOR SEQUENCE MANIPULATION; U.S. application 62/098,059, Dec. 30, 2014, 62/181,641, Jun. 18, 2015, and 62/181,667, Jun. 18, 2015, RNA-TARGETING SYSTEM; U.S. application 62/096,656, Dec. 24, 2014 and 62/181,151, Jun. 17, 2015, CRISPR HAVING OR ASSOCIATED WITH DESTABILIZATION DOMAINS; U.S. application 62/096,697, Dec. 24, 2014, CRISPR HAVING OR ASSOCIATED WITH AAV; U.S. application 62/098,158, Dec. 30, 2014, ENGINEERED CRISPR COMPLEX INSERTIONAL TARGETING SYSTEMS; U.S. application 62/151,052, Apr. 22, 2015, CELLULAR TARGETING FOR EXTRA-CELLULAR EXOSOMAL REPORTING; U.S. application 62/054,490, Sep. 24, 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, Feb. 12, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, Sep. 25, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, Dec. 4, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, Sep. 24, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, Oct. 23, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, Sep. 24, 2014 and 62/181,002, Jun. 17, 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, Sep. 24, 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, Sep. 25, 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, Sep. 25, 2014, MULTIFUNCTIONAL-CRISPR COMPLEXES AND/OR OPTIMIZED ENZYME LINKED FUNCTIONAL-CRISPR COMPLEXES; U.S. application 62/087,475, Dec. 4, 2014 and 62/181,690, Jun. 18, 2015, FUNCTIONAL SCREENING WITH OPTIMIZED FUNCTIONAL CRISPR-CAS SYSTEMS; U.S. application 62/055,487, Sep. 25, 2014, FUNCTIONAL SCREENING WITH OPTIMIZED FUNCTIONAL CRISPR-CAS SYSTEMS; U.S. application 62/087,546, Dec. 4, 2014 and 62/181,687, Jun. 18, 2015, MULTIFUNCTIONAL CRISPR COMPLEXES AND/OR OPTIMIZED ENZYME LINKED FUNCTIONAL-CRISPR COMPLEXES; and U.S. application 62/098,285, Dec. 30, 2014, CRISPR MEDIATED IN VIVO MODELING AND GENETIC SCREENING OF TUMOR GROWTH AND METASTASIS.

Mention is made of U.S. applications 62/181,659, Jun. 18, 2015 and 62/207,318, Aug. 19, 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, Jun. 18, 2015 and 62/245,264, Oct. 22, 2015, NOVEL CRISPR ENZYMES AND SYSTEMS, U.S. applications 62/181,675, Jun. 18, 2015, 62/285,349, Oct. 22, 2015, 62/296,522, Feb. 17, 2016, and 62/320,231, Apr. 8, 2016, NOVEL CRISPR ENZYMES AND SYSTEMS, U.S. application 62/232,067, Sep. 24, 2015, U.S. application Ser. No. 14/975,085, Dec. 18, 2015, European application No. 16150428.7, U.S. application 62/205,733, Aug. 16, 2015, U.S. application 62/201,542, Aug. 5, 2015, U.S. application 62/193,507, Jul. 16, 2015, and U.S. application 62/181,739, Jun. 18, 2015, each entitled NOVEL CRISPR ENZYMES AND SYSTEMS and of U.S. application 62/245,270, Oct. 22, 2015, NOVEL CRISPR ENZYMES AND SYSTEMS. Mention is also made of U.S. application 61/939,256, Feb. 12, 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, Aug. 15, 2015, U.S. application 62/180,699, Jun. 17, 2015, and U.S. application 62/038,358, Aug. 17, 2014, each entitled GENOME EDITING USING CAS9 NICKASES.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, and of PCT application PCT/US14/70127, entitled "DELIVERY, USE AND THERAPEUTIC APPLICATIONS OF THE CRISPR-CAS SYSTEMS AND COMPOSITIONS FOR GENOME EDITING" (claiming priority from one or more or all of US provisional patent applications: 61/915,176; 61/915,192; 61/915,215; 61/915,107, 61/915,145; 61/915,148; and 61/915,153 each filed Dec. 12, 2013) ("the Eye PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30 C, e.g., 20-25 C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing.

As also set forth in greater detail elsewhere herein, application of the methods of the instant disclosure to detection of off-target nicks and therefore off-target sites of gene editing (which are potentially highly deleterious to clinical applications of gene edited cells) is expressly contemplated.

Off-Target Effects of CRISPR/Cas9 Gene Editing

CRISPR/Cas9 gene editing approaches have been previously described to possess off-target activities that are capable of hampering certain clinical applications of such gene editing approaches. Zhang et al. reviewed some such off-target effects in Molecular Therapy: Nucleic Acids 4: e264, while U.S. Patent Application No. 2018/0068062 identified the following examples of off-target CRISPR/Cas9 effects:

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors found that SpCas9 tolerated mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and gRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Because the combination of high on-target mutation rates accompanied by an absence of off-target mutations is desirable in performing CRISPR/Cas-mediated gene editing approaches, the methods of the instant disclosure are contemplated as especially useful for screening of cells subjected to CRISPR/Cas gene editing to identify sites of off-target nicks and/or screening of sgRNAs for those sgRNAs that exert relatively low levels of off-target impact (and ideally no off-target impacts), as compared to other tested sgRNAs.

Therapeutic Agents

As used herein, therapeutic agents are agents that ameliorate the symptoms of a disease or disorder or ameliorate the disease or disorder. Therapeutic agents can be any molecule, such as a small molecule, a peptide, a polypeptide, a protein, an antibody, an antibody fragment, a DNA, or a RNA. Therapeutic agent, therapeutic compound, or therapeutic regimens include conventional drugs and drug therapies, including vaccines for treatment or prevention (i.e., reducing the risk of getting a particular disease or disorder), which are known to those skilled in the art and described elsewhere herein. Therapeutic agents for the treatment of neoplastic disease include, but are not limited to, moieties that inhibit cell growth or promote cell death, that can be activated to inhibit cell growth or promote cell death, or that activate another agent to inhibit cell growth or promote cell death. Therapeutic agents for use in the methods provided herein can be, for example, an anticancer agent. Exemplary therapeutic agents include, for example, therapeutic microorganisms, such as therapeutic viruses and bacteria, chemotherapeutic compounds, cytokines, growth factors, hormones, photosensitizing agents, radionuclides, toxins, antimetabolites, signaling modulators, anticancer antibiotics, anticancer antibodies, anti-cancer oligopeptides, anticancer oligonucleotide (e.g., antisense RNA and siRNA), angiogenesis inhibitors, radiation therapy, or a combination thereof.

As used herein, an anti-cancer agent or compound (used interchangeably with "anti-tumor or anti-neoplastic agent") refers to any agents, or compounds, used in anti-cancer treatment. These include any agents, when used alone or in combination with other compounds or treatments, that can alleviate, reduce, ameliorate, prevent, or place or maintain in a state of remission of clinical symptoms or diagnostic markers associated with neoplastic disease, tumors and cancer, and can be used in methods, combinations and compositions provided herein.

Chemotherapeutics

As used herein, a "chemotherapeutic agent" is any drug or compound that is used in anti-cancer treatment. Exemplary of such agents are alkylating agents, nitrosoureas, antitumor antibiotics, antimetabolites, antimitotics, topoisomerase inhibitors, monoclonal antibodies, and signaling inhibitors. Exemplary chemotherapeutic agent include, but are not limited to, chemotherapeutic agents, such as Ara-C, cisplatin, carboplatin, paclitaxel, doxorubicin, gemcitabine, camptothecin, irinotecan, cyclophosphamide, 6-mercaptopurine, vincristine, 5-fluorouracil, and methotrexate. The term "chemotherapeutic agent" can be used interchangeably with the term "anti-cancer agent" when referring to drugs or compounds for the treatment of cancer. As used herein, reference to a chemotherapeutic agent includes combinations or a plurality of chemotherapeutic agents unless otherwise indicated.

As used herein, an anti-metastatic agent is an agent that ameliorates the symptoms of metastasis or ameliorates metastasis. Generally, anti-metastatic agents directly or indirectly inhibit one or more steps of metastasis, including but not limited to, degradation of the basement membrane and proximal extracellular matrix, which leads to tumor cell detachment from the primary tumor, tumor cell migration, tumor cell invasion of local tissue, tumor cell division and colonization at the secondary site, organization of endothelial cells into new functioning capillaries in a tumor, and the persistence of such functioning capillaries in a tumor. Anti-metastatic agents include agents that inhibit the metastasis of a cell from a primary tumor, including release of the cell from the primary tumor and establishment of a secondary tumor, or that inhibits further metastasis of a cell from a site of metastasis. Treatment of a tumor bearing subject with anti-metastatic agents can result in, for example, the delayed appearance of secondary (i.e. metastatic) tumors, slowed development of primary or secondary tumors, decreased occurrence of secondary tumors, slowed or decreased severity of secondary effects of neoplastic disease, arrested tumor growth and regression.

Antibiotics and Antimycotics

Exemplary antibiotics for use in certain methods of the instant disclosure include any antibiotic that reduces the number or amount of commensal gut bacteria. These include, but are not limited to, penicillins, penicillin combinations, cephalosporins, tetracyclines, β-lactam antibiotics, carbacephems, glycopeptides, aminoglycosides, ansamycins, macrolides, monobactams, nitrofurans, sulfonamides, lincosamides, lipopeptides, polypeptides, quinolones, drugs against mycobacteria, oxazolidinones, arsphenamine, chloramphenicol, fosfomycin, fusidic acid, metronidazole, tazobactam, mupirocin, platensimycin, quinupristin/dalfopristin, thiamphenicol, tigecycline, tinidazole and trimethoprim and mixtures thereof. The antibiotic can be selected from among penicillin, benzylpenicillin (penicillin G), procaine benzylpenicillin (procaine penicillin), benzathine benzylpenicillin (benzathine penicillin), phenoxymethylpenicillin (penicillin V), amoxicillin, ampicillin, azlocillin, carbenicillin, cloxacillin, dicloxacillin, flucloxacillin, mezlocillin, methicillin, nafcillin, oxacillin, temocillin, ticarcillin, amoxicillin/clavulanate, ampicillin/sulbactam, piperacillin/tazobactam, ticarcillin/clavulanate, demeclocycline, doxycycline, minocycline, oxytetracycline, tetracycline, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefmetazole, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, cefaloram, cefaparole, cefcanel, cefedrolor, cefempidone, cefetrizole, cefivitril, cefmepidium, cefoxazole, cefrotil, cefsumide, ceftioxide, cefuracetime, ertapenem, doripenem, imipenem, imipenem/cilastatin, meropenem, panipenem/betamipron, biapenem, razupenem, tebipenem, loracarbef, teicoplanin, vancomycin, bleomycin, ramoplanin, decaplanin, telavancin, streptomycin, gentamicin, kanamycin, neomycin, netilmicin, tobramycin, spectinomycin, paromomycin, framycetin, ribostamycin, amikacin, arbekacin, bekanamycin, dibekacin, rhodostreptomycin, apramycin, hygromycin B, paromomycin sulfate, sisomicin, isepamicin, verdamicin, astromicin, geldanamycin, herbimycin, rifaximin, azithromycin, clarithromycin, dirithromycin, erythromycin, roxithromycin, telithromycin, carbomycin A, josamycin, kitasamycin, midecamycin, midecamycin acetate, oleandomycin, solithromycin, spiramycin, troleandomycin, tylosin, tylocine, ketolides such as telithromycin, cethromycin, solithromycin, spiramycin, ansamycin, oleandomycin, carbomycin, tylosin, aztreonam, furazolidone, nitrofurantoin, mafenide, sulfamethoxazole, sulfisomidine, sulfadiazine, silver sulfadiazine, sulfamethoxine, sulfamethizole, sulfanilamide, sulfasalazine, sulfi soxazole, trimethoprim-sulfamethoxazole, sulfonamidochrysoidine, sulfacetamide, sulfadoxine, dichlorphenamide, clindamycin, lincomycin, daptomycin, bacitracin, colistin, polymyxin B, moxifloxacin, ciprofloxacin, levofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, pazufloxacin, sparfloxacin, tosufloxacin, clinafloxacin, gatifloxacin, gemifloxacin, moxifloxacin, sitafloxacin, trovafloxacin, prulifloxacin, clofazimine, dapsone, capreomycin, cycloserine, ethambutol, ethionamide, isoniazid, pyrazinamide, rifampicin, rifabutin, rifapentine, streptomycin, linezolid, posizolid, radezolid, cycloserine, torezolid, arsphenamine, chloramphenicol, fosfomycin, fusidic acid, metronidazole, tazobactam, mupirocin, platensimycin, quinupristin/dalfopristin, thiamphenicol, tigecycline, tinidazole and trimethoprim and mixtures of any of the antibiotics. Particular antibiotics include penicillin, streptomycin, ampicillin, neomycin, metronidazole, vancomycin, tazobactam, meropenem, a mixture of penicillin and streptomycin, a mixture of ampicillin, neomycin, metronidazole and vancomycin, and a mixture of tazobactam, meropenem and vancomycin.

Exemplary antimycotics for use in certain methods of the instant disclosure include, but are not limited to, amphotericin B, candicidin, filipin, hamycin, natamycin, nystatin, rimocidin, imidazole antifungals, bifonazole, butoconazole, clotrimazole, econazole, fenticonazole, isoconazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfine, butenafine, naftifine, terbinafine, anidulafungin, caspofungin, micafungin, ciclopirox, flucytosine, 5-fluorocytosine, griseofulvin, haloprogin, polygodial, tolnaftate, undecylenic acid and crystal violet.

It is expressly contemplated that therapeutic agents of the instant disclosure can be used alone or in combination with each another, e.g., for purpose of identifying the effect of contacting organisms/cells with such agents, specifically for detecting SSB prevalence and/or SSB location(s).

Kits

The instant disclosure also provides kits containing agents of this disclosure for use in the methods of the present disclosure. Kits of the instant disclosure may include one or more containers comprising a purified agent (e.g., DNA polymerase I, dKTP and/or dPTP) of this disclosure and/or may contain agents for biotin-streptavidin-mediated pulldowns, amplifying and/or sequencing DNA fragments derived from DNA sequences upon which polymerase has acted to incorporate one or more nucleotide analogs. In some embodiments, the kits further include instructions for use in accordance with the methods of this disclosure. In some embodiments, these instructions comprise a description of administration of the agent to identify one or more sites of single-stranded break, according to any of the methods of this disclosure. In some embodiments, the instructions comprise a description of how to detect a single-stranded break, for example in an individual, in a tissue sample, or in a cell. The kit may further comprise a description of selecting an organism and/or dsDNA-containing system suitable for assessment of single-stranded break location(s).

The instructions generally include information as to agent concentrations, timing, etc. for the intended SSB-detecting diagnostics. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Template Preparation for Nicking

Annealed oligonucleotides were used for studies on the mutagenic potential of dPTP and dKTP. Briefly, three oligonucleotides were ordered from Integrated DNA Technologies (IDT) sized X, Y and Z. The bottom strand was kept constant, while the two top oligonucleotides were annealed by incubating 100 µM of DNA from 95° C. to 25° C. at 0.1° C./sec and holding at 88, 74, 60 and 37° C. for 2 min each. The location of the nick was created at multiple locations to compare the effect of incorporating Ps and Ks opposite any of the four natural bases. All oligonucleotides were purchased from IDT as standard desalted oligonucleotides. A plasmid containing two was nick sites that were artificially created using the nicking enzyme Nb.BsmI obtained from New England Biolabs. The manufacturers protocol was followed to generate nicks. Briefly made fresh, the enzyme, template, and NEB buffer 3.1 was incubated at 65° C. for 1 hr followed by heat inactivation at 85° C. for 20 min and stored at 4° C.

Incorporation of Nucleotide Analogs and Biotinylated dUTP

Nick translation reactions were set up with dPTP (Trilink Biotechnologies) and dKTP (Axxora, Inc) at concentrations ranging from 100 nM to 1 and were incubated with 1 unit of Taq polymerase in thermoPol buffer and incubated at 72° C. for 5 to 30 min. The unincorporated nucleotides were removed by 1:1 SPRI (Agentcourt) and the DNA was resuspended in TE buffer. Next, nick translation with a 20% solution of Biotin 11-dUTP (Life Technologies) in standard dNTPs at 40 nM were incubated with 1 unit of Taq polymerase in thermoPol buffer for 30 min. The DNA template was washed again with a 1:1 SPRI and resuspended in TE buffer.

Custom Transposome Assembly

Transposases were expressed, purified, and assembled following methods published previously. DNA containing unique molecular identifiers (UMI), custom read 1 and read 2 sequences and the 19 bp mosaic end were annealed by incubating 100 µM of DNA from 95° C. to 25° C. at 0.1° C./sec and holding at 88, 74, 60 and 37° C. for 2 min each. The annealed oligos and transposases were mixed at 12.5 µM and incubated at 37° C. for 1 hour before storing at −20° C.

Targeted Pulldown and Library Construction

The DNA was tagmented with Nextera™ (Illumina™) at 55° C. for 10 min followed with 0.1% SDS treatment to dissociate the transposase from the DNA. Streptavidin myOne™ Dynabeads™ were washed according to the manufacturer's protocol and incubated with the purified DNA above for 30 min at room temperature with agitation. The beads were washed with the manufacturer's binding and washing buffer supplemented with 0.1% TWEEN to prevent aggregation and improve DNA recovery. Three washes were performed to remove any non-biotinylated DNA. The beads were diluted and added to a PCR using Taq polymerase and barcoded with P5 and P7 primers at 0.5 PCR was performed for 30 cycles and the final product was confirmed on an agarose gel. The PCR product was then purified with 1:1 SPRI (Agentcourt) and quantified with the Qubit assay (Qiagen™).

Sequencing

Target-enriched NickSeq libraries were loaded at 1.5 pM on an Illumina™ Miniseg™ with a 150 cycle kit. Primary processing of the raw data was conducted using cutadapt to ensure no adapters remained, bowtie2 to align the reads to the reference sequence and samtools to create a sorted, indexed BAM file. Secondary analyses were carried out using custom Python scripts. The custom scripts used for secondary analysis can be found at github.com/nranu/Nick-Seq.

Secondary Computational Analysis

Sequencing peak position and ranges across the template was called with a ChIP Seq peak caller, MACs2. Sites of interest were ranked by p value for further analysis. Pysam was used to parse bam files in the peak regions called by MACs. At each base position, the majority base was used to predict which base (P or K) would be incorporated, and then the fraction of the expected minority base was determined. A P-value was assigned for every base in a 5 bp sliding window to find the region that had a mutational signature.

Receiver Operator Characteristic (ROC) and Sensitivity Analysis

The positive sample was spiked with increasing noise from the negative control. The empirically determined enrichment factor was used to determine what fraction of nicks could exist in the original sample to give the in silico determined sequencing profile. The ROC curve for peak region identification was created by thresholding on each SSB fraction generated sample. For each SSB fraction, the frequency of the expected at the 5' most position of the break was plotted to assess sensitivity.

Example 2: "NickSeq" Precisely Identified Single-Stranded Break Positions Using Degeneracy-Producing Nucleotide Analogs, Tagged Nucleotides and Next-Generation Sequencing Single-stranded breaks in genomic DNA have been posited to be associated with certain types of human disease (FIG. 1), particularly neurological disorders and disease (e.g., neurological deficits in AOA-1 have been identified as likely the result of accumulating unrepaired single-stranded breaks specifically in neurons (Ahel et al. Nature 443: 713-16, as cited by O'Driscoll M. Cold Spring Harb Perspect Biol 2012; 4: a012773)). Single-stranded breaks (SSBs) are the most common types of break to occur in genomic DNA, arising at a frequency of tens of thousands per cell per day from direct attack by intracellular metabolites and from spontaneous DNA decay.

Figure 2A:
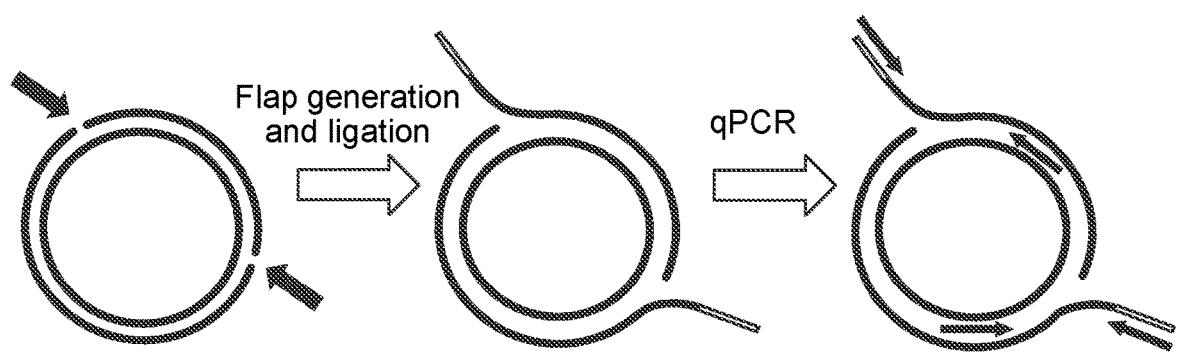
FIGS. 2A to 2C show that an art-recognized adapter ligation method located nicks (single-stranded breaks) with only low efficiency (specifically, only 1 in 500 nick locations were correctly identified through next generation sequencing), as well as high background.
Figure 2B:
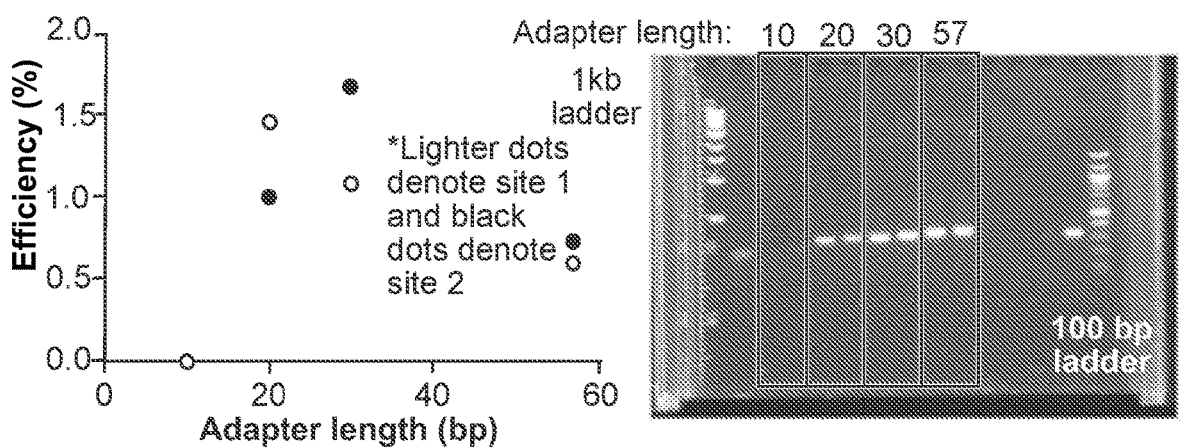
Figure 2C:
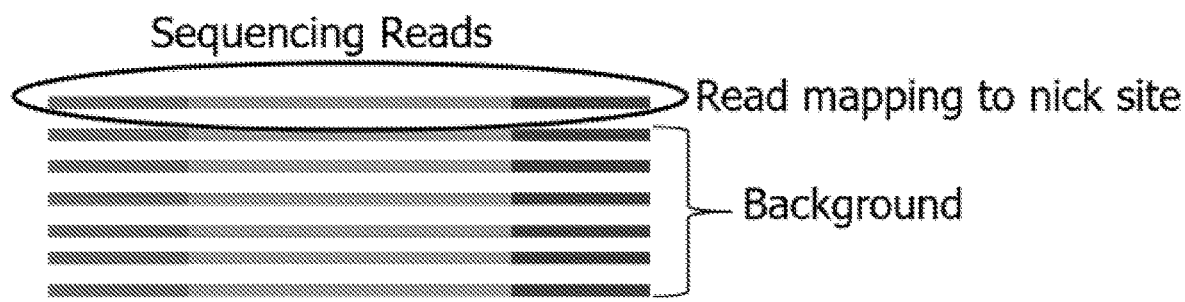

Identification of single-stranded breaks in double-stranded DNA (dsDNA) has previously been performed with only low efficiency, and with low precision regarding the location of a particular site of a single-stranded break (thereby making it extremely difficult to identify any single-stranded break "hotspots" that might exist, e.g., in the mammalian genome). As shown in FIGS. 2A to 2C, an art-recognized adapter ligation method has been used to locate nicks (single-stranded breaks) with only low efficiency (specifically, only 1 in 500 nick locations were correctly identified through performance of this approach in concert with next generation sequencing), as well as high background. Such an approach was tested upon a plasmid harboring two nick (single-stranded break) sites generated by the nicking restriction enzyme Nb.BsmI (FIG. 2A), with flaps generated at the nick site using Vent (exo-), and a sequencing adapter (shown in lighter color at 5' ends) ligated to the 5' end of the flap using T4 RNA ligase. Efficiency was measured via qPCR by taking the fraction of adapters bound to total plasmid in the sample, and initial confirmation of results was performed via Sanger sequencing. In particular, the location of nick sites was identified with only 0.5-1.5% efficiency via qPCR (FIG. 2B), with efficiency varying dependent on adapter length. QPCR products were confirmed via gel electrophoresis on a 1% agarose gel. As shown in FIG. 2C, next-generation sequencing (NGS) results showed low specificity, as most reads did not map to the nick site. Thus, an improved method—compatible with next-generation sequencing approaches—was desired for single-stranded break detection in dsDNA.

Figure 3:
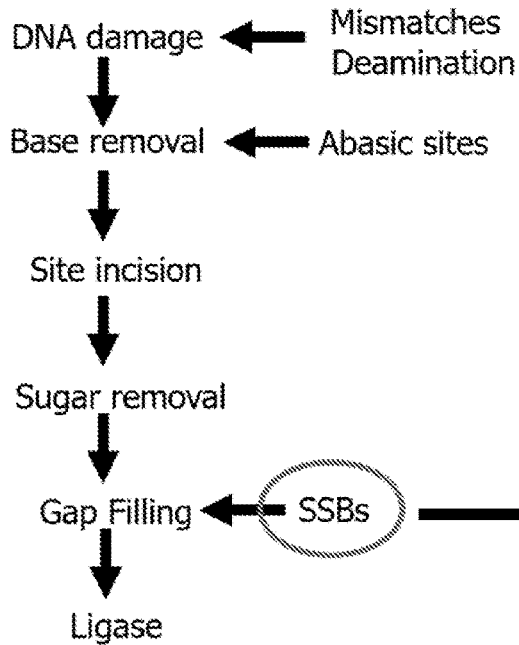
FIG. 3 shows how the instant method fits into the process of base excision repair.
Figure 3:

The instant method was designed to locate single-stranded breaks at the site at which gap filling would occur during the native DNA base excision repair process (FIG. 3). Termed "NickSeq", the instant method employs incorporation of both a degeneracy-producing nucleotide analog (i.e., a "universal" and/or otherwise degenerate/"wobble" base-effecting nucleotide) and a tagged nucleotide during DNA polymerase I-mediated strand extension, where the tagged nucleotide provides a tag that can be bound and isolated, thereby allowing for isolation of DNA fragments in a region surrounding the site(s) of a single-stranded break, and the "universal" and/or otherwise degenerate/"wobble" base-effectinf nucleotide (the nucleotide analog that produces a degenerate sequence during amplification) produces a distinct signal during sequencing (including during next-generation sequencing) that reflects the precise location of a single-stranded break in the isolated dsDNA.

Figure 5:
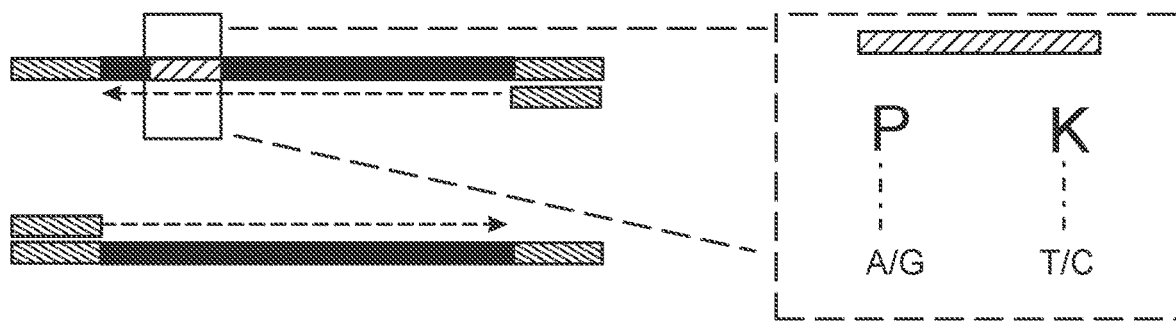
FIG. 5 shows that nucleotide analogs that produce a degenerate site during complementary strand extension (e.g., dPTP and dKTP) gave rise to a unique signal when library molecules were amplified by taq polymerase in their presence.

The instant approach takes advantage of the behavior of templates containing universal base pairs during PCR. Universal bases have the property of base pairing with two or more of the canonical bases (Hill 1998). Herein, the universal bases 6H,8H-3,4-dihydropyrimido[4,5-c][1,2]oxazin-7-one (P) and N6-methoxy-2,6-diaminopurine (K) were introduced at the 3' end of a SSB through nick translation. P base pairs with A and G, whereas K base pairs with T and C through similar hydrogen bonding as the canonical bases (Hill 1998) (FIG. 4). This characteristic allowed for the incorporation of the universal pyrimidine, P, and the universal purine, K, into DNA through nick translation at the site of damage (FIG. 4). Biotinylated dUTP was then added downstream of the Ps and Ks through a second nick translation (FIG. 4). The libraries were then selectively enriched for SSBs through capture of biotinylated dUTP on streptavidin beads (FIG. 4). Library preparation through tagmenation and PCR with this resulting template and standard dNTPs resulted in each P and K position having a unique distribution of the canonical bases (FIG. 4, lower panel). Next generation sequencing of the resulting DNA library then showed (as demonstrated below) a consecutive set of variants originating from the start of the SSB.

dPTP base pairs with either adenine or guanine during extension of a paired strand during amplification, at a proportion of approximately 60% adenine and 40% guanine in prevalence of incorporation. Similarly, dKTP base pairs with either thymine or cytosine during extension of a paired strand during amplification, at a proportion of approximately 85% thymine and 15% cytosine in prevalence of incorporation (FIG. 5).

Biotin-tagged dsDNA was then fragmented to an average fragment size of 300-500 bp, and streptavidin was employed in a biotin pulldown procedure, to specifically bind and isolate biotin-tagged dsDNA fragments from the fragmented population of dsDNAs. An exogenous nucleotide sequence was then end-ligated to the isolated dsDNA fragments (per the Illumina™ protocol, one end received read 1 and the mosaic end, while the other end received reads 2 and the mosaic end for TN5), and PCR amplification was performed via annealing of amplification primers to such end-ligated sequences. Following PCR amplification, next-generation sequencing of individual dsDNA fragment strands was performed (Nextera™ tagmentation was performed, followed by sequencing on a Miniseq™ with a 150 cycle kit).

Figure 6:
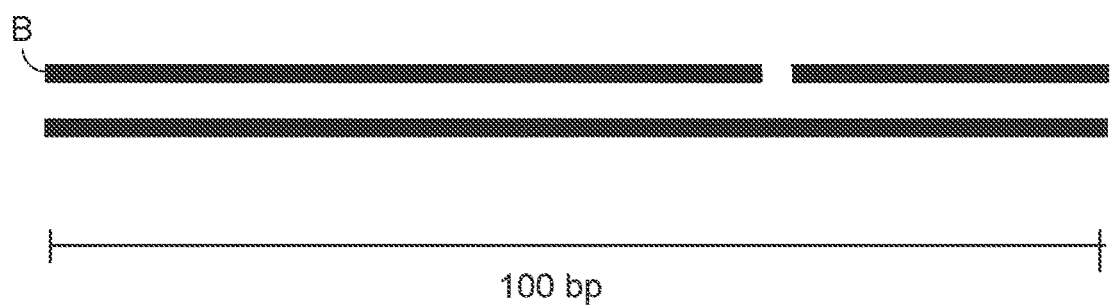
FIG. 6 shows a proof of concept experiment that was performed upon annealed oligonucleotides creating a nick structure.
Figure 6:
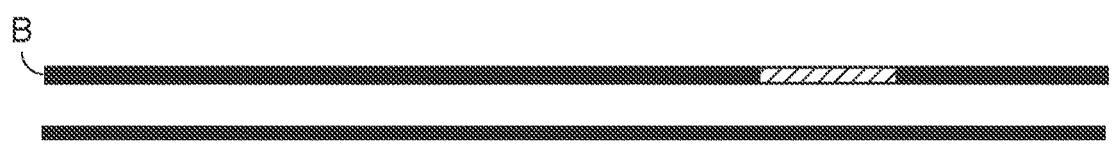
Figure 7A:
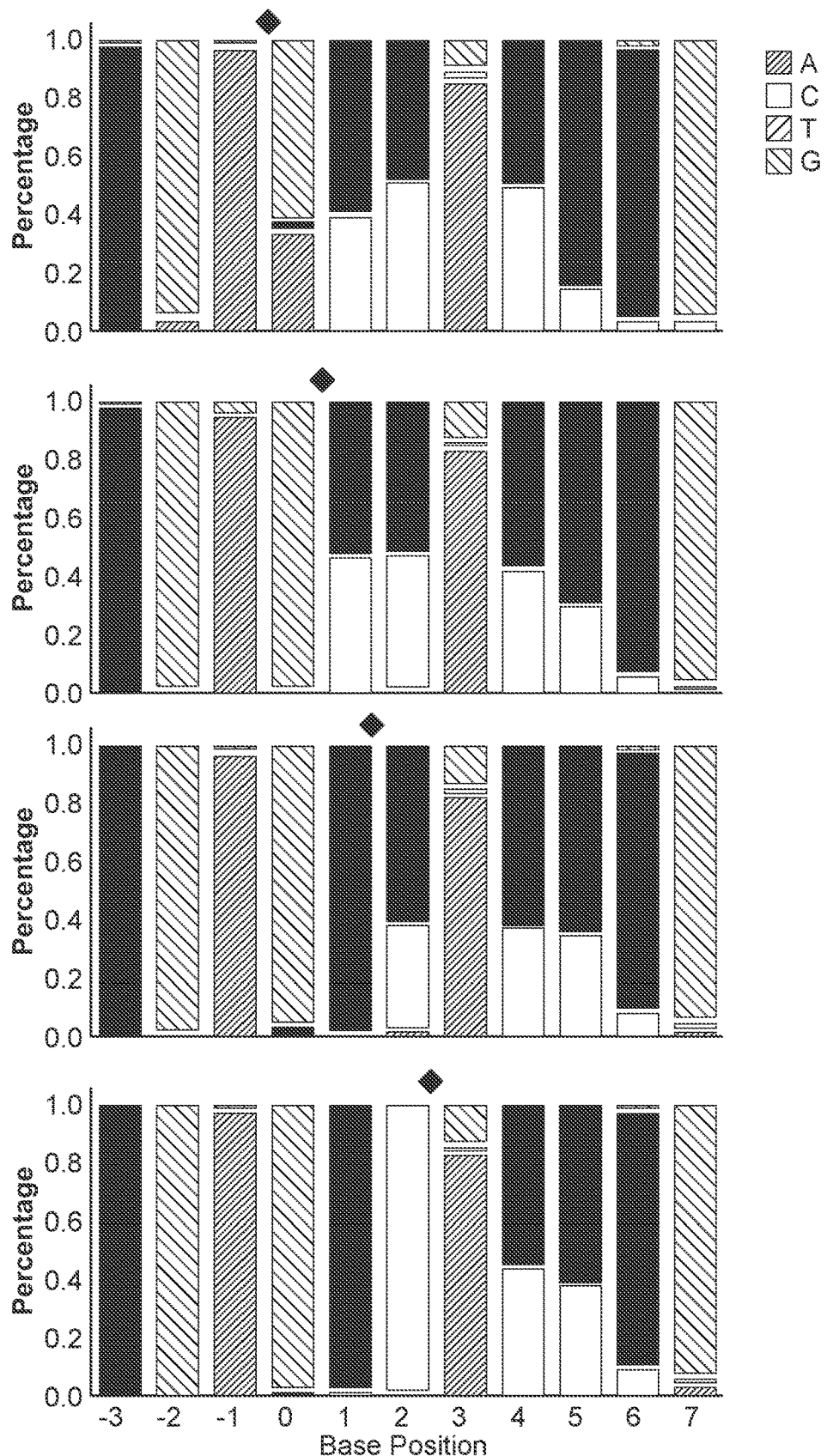
FIGS. 7A and 7B show the mutational characteristics of dPTP and dKTP that occurred when amplified by two different polymerases.
Figure 7B:
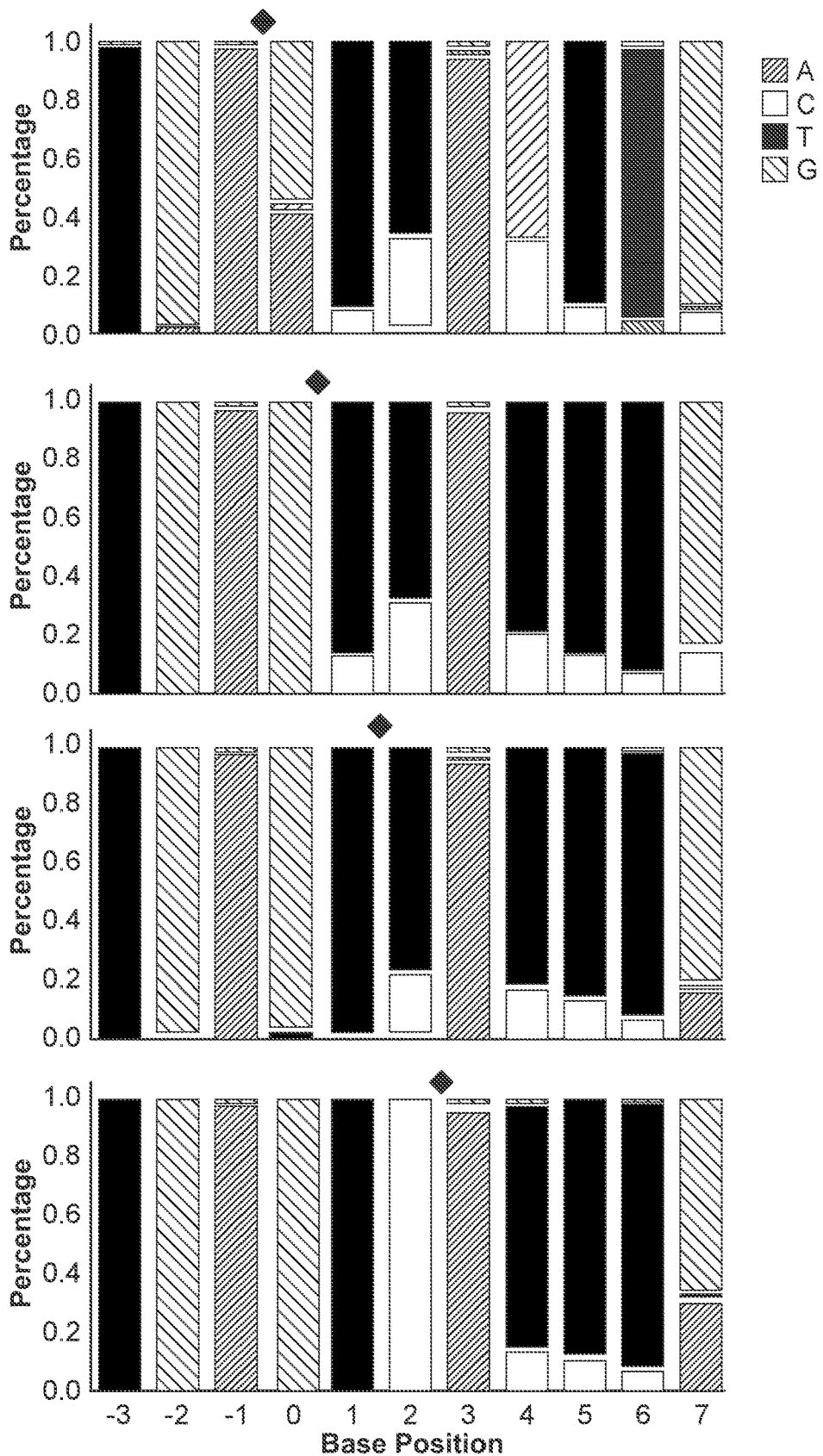

In an initial proof-of-concept test of the above-described process, an end-biotinylated primer of 100 nucleotides in length was synthesized and annealed to its complement, thereby generating a dsDNA of 100 base pairs in length (FIG. 6). The biotinylated strand was nicked by the nicking restriction enzyme Nb.BsmI, and nick translation in the presence of dPTP and dKTP was then performed. To determine how these universal bases behaved in PCR, the mutational signal that arose when templates containing dPTP and dKTP were amplified through PCR with two polymerases was determined (FIGS. 7A and 7B). Custom oligonucleotides were annealed such that the SSB would occur at each of the four canonical bases, A, C, T and G, and dPTP and dKTP were then incorporated (FIGS. 7A and 7B). As shown in FIGS. 7A and 7B, the ratio of T:C (85:15) and A:G (60:40) for dKTP and dPTP respectively was consistent with the literature (Hill 1998), and incorporation of dPTP and dKTP residues created regions of amplified sequence that exhibited degenerate base-calls. The mutational signature arising due to PCR with dPTP and dKTP resulted in a distinct signature directly at the 5' most base next to the break site. In particular, a decaying stretch of apparent heterozygosity (created by alternative base incorporation during polymerase-mediated extension of sequences annealing to degeneracy-producing nucleotide analogs (e.g., dPTP and/or dKTP)-containing sequences) was observed. It was hypothesized that the P's and K's would be added to the nascent DNA strand until the double stranded helix grew unstable due to the inherent instability of incorporating non-natural nucleic acids. The extension added about 4-7 nucleotides of P's and K's when thresholding the variant calling at 1%, and can typically occur across four, five, six or even more (e.g., ten or twelve, or more) oligonucleotide residues. Thus, dPTP and dKTP created a unique mutational signature when incorporated into templates amplified by PCR.

Figure 8:
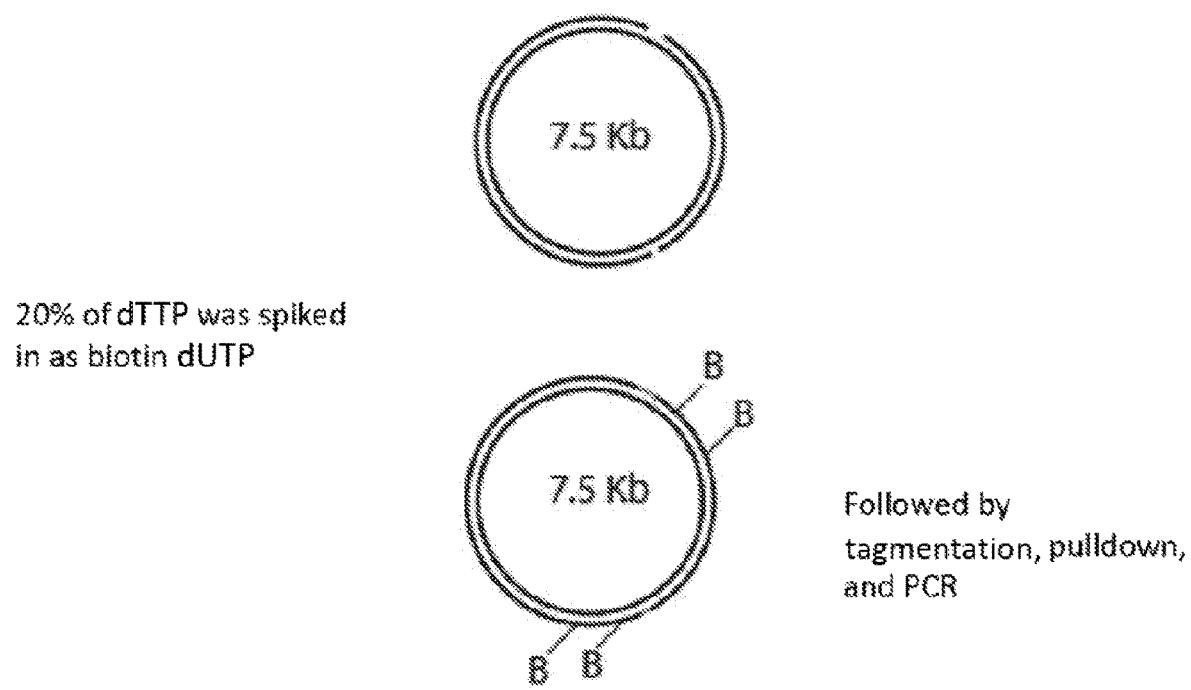
FIG. 8 shows a diagram of a proof-of-concept experiment in which a 7.5 Kb plasmid was nicked at two known locations with a restriction nicking enzyme, and the instant "NickSeq" process was then performed.
Figure 9A:
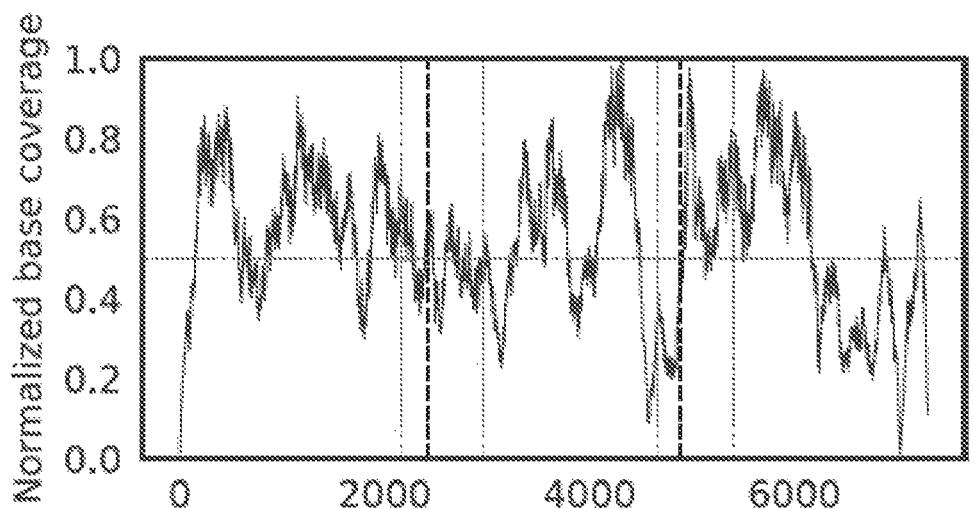
FIGS. 9A and 9B show the enrichment of nicked locations obtained on an 8 kb plasmid.
Figure 9B:
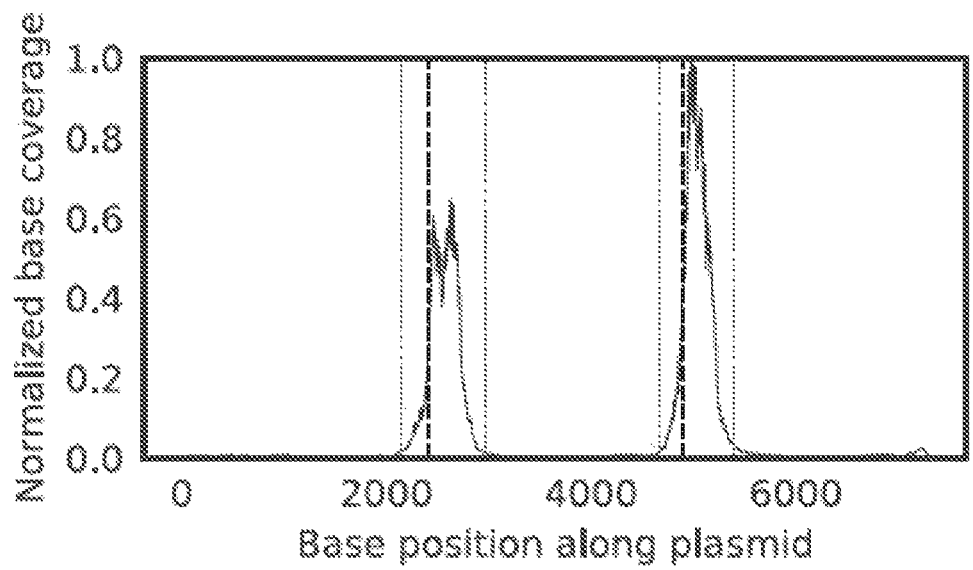
Figure 10:
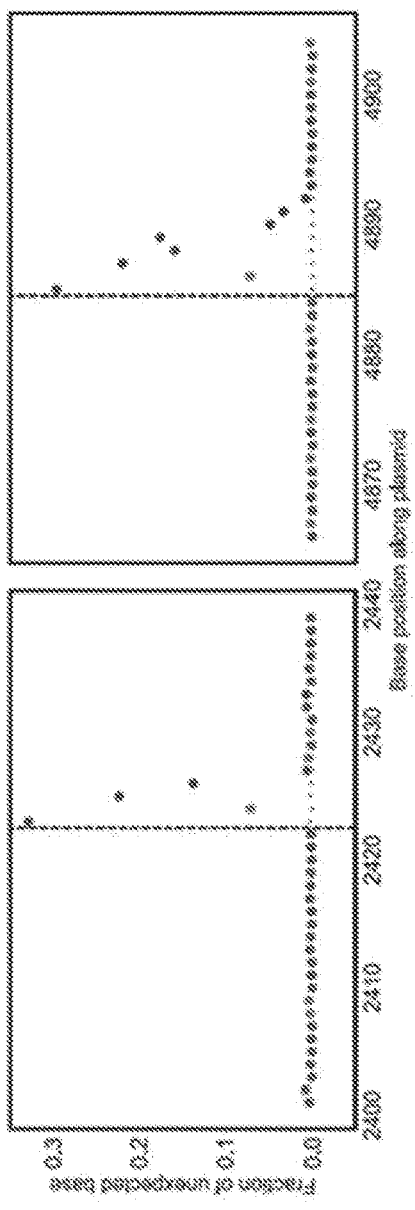
FIG. 10 shows a closer look at the two nick locations of FIGS. 8 and 9, which exhibited a sequence of bases marked by presence of a degenerate base (reflective of nick translation-mediated incorporation of a nucleotide analog), with signal decreasing as distance from the nick site increased.
Figure 11:
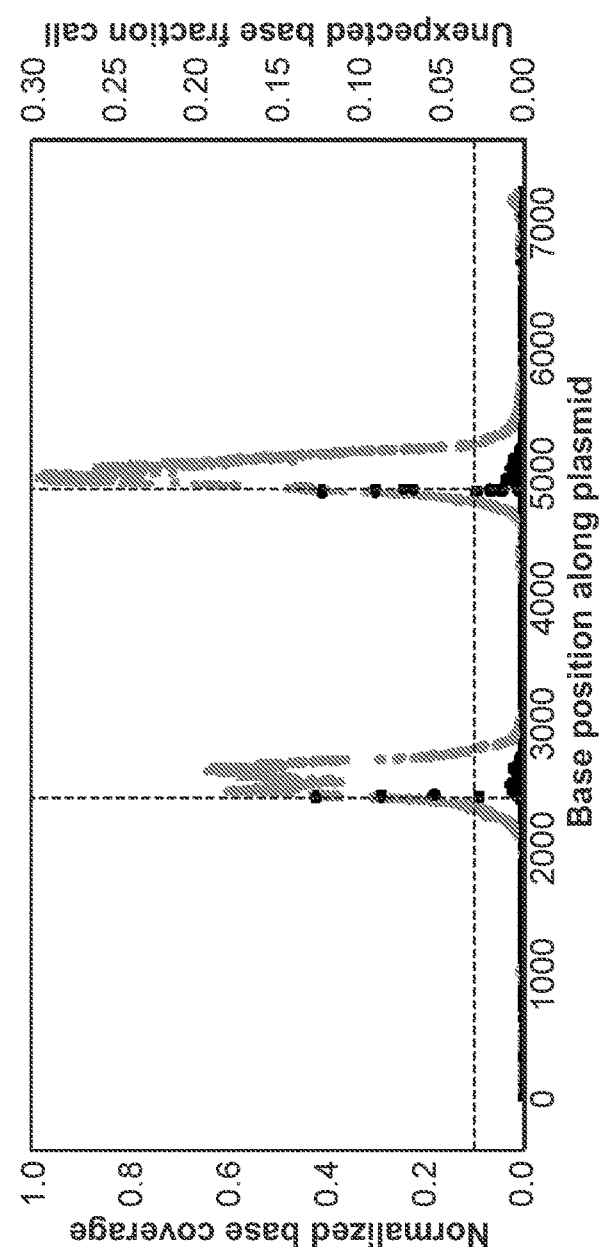
FIG. 11 shows that the strand that the nick occurred upon could also be determined by comparing the position of the degenerate signal to the sequencing peak, noting that sequences surrounding the nicked regions are displayed at bottom (displayed sequences are: 5'-CGCAGGPKPPPPPPCTCCGC-3' SEQ ID NO: 1; 5'-GCGGAGGGGGAATGCCTGCG-3' SEQ ID NO: 2: 5'-CGCAGGCATTCCCCCTCCGC-3' SEQ ID NO: 3; and 5'-GCGGAGKKKKKKPKCCTGCG-3', SEQ ID NO: 4).
Figure 12:
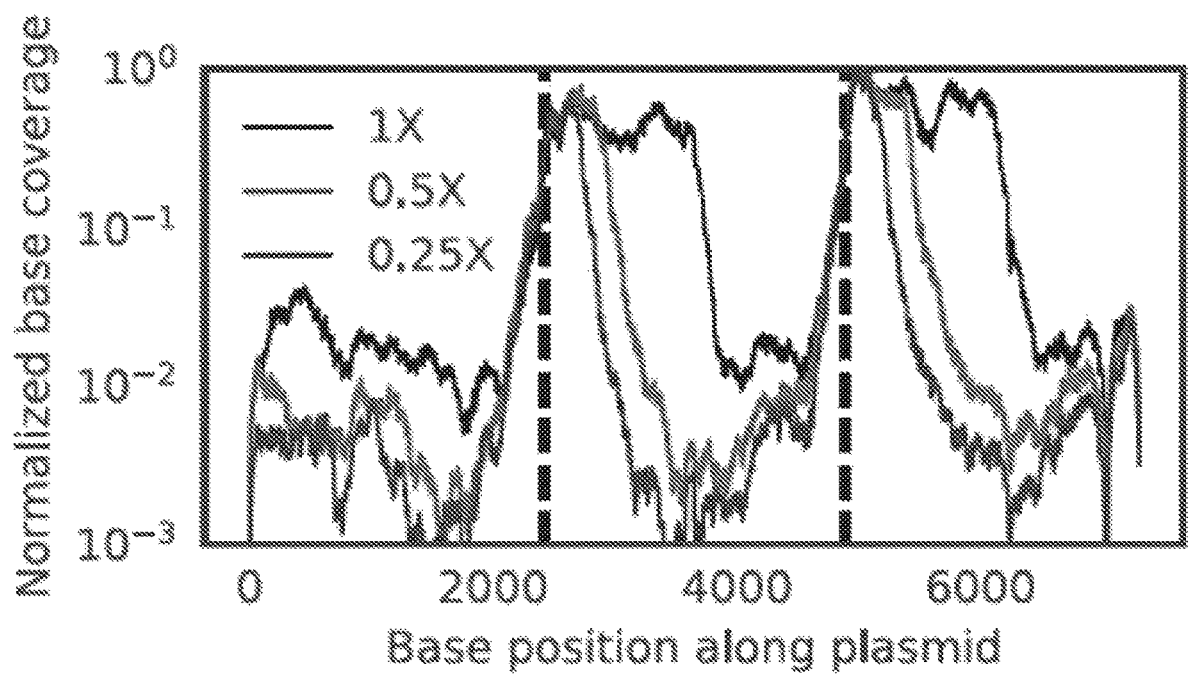
FIG. 12 shows that peak width of single-stranded break signal could be controlled by altering the concentration of dNTPs and biotin UTP. In particular, decreasing the total concentration of dNTPs reduced the length of extension such that the width of the peaks around the SSB could be modulated. 1× is defined at 160 nM of dNTPs+32 nM of biotin-11-dUTP.

In a further proof-of-concept experiment, a 7.5 Kb plasmid was nicked at two known locations with a restriction nicking enzyme, and the instant "NickSeq" process was then performed (FIG. 8), including a step of incorporating biotinylated nucleotides during nick translation, then performing biotin pulldowns, PCR amplification and sequencing. It was identified that molecules that contained dPTP and dKTP could be enriched through pulldown with biotin UTP. As shown in FIGS. 9A and 9B, a targeting approach was designed to selectively sequence the molecules of DNA that contained Ps and Ks by adding an antigen, biotin, through a second nick translation with dNTPs and biotinylated dUTPs. The resulting sequencing reads were enriched ~1000 fold for the locations at which the nicks occurred through a pull down with streptavidin beads. In particular, when this procedure was performed upon the twice-nicked plasmid, two obvious peaks were observed. (While certain background signal was observed in FIG. 8 during this experiment, two simple options are readily available and expressly contemplated to improve this: in particular, the concentration (amount of biotin incorporated) can be further optimized (too much can increase background) and polymerase optimization can also have profound impact upon adding biotin dUTP to the P and K sequence; in addition, there are also a set of different molecules that could be used to perform the pulldown other than biotin.) Closer examination of sequence at the two nick locations of the plasmid revealed a series of bases marked by presence of a degenerate base, with signal decreasing as distance from the nick site increased (FIG. 10). The instant approach allowed for determination of the precise location of the nick, including the strand upon which the original nick occurred, as comparison of the position of the degenerate signal to the sequencing peak revealed the location (at the start of the series of degenerate bases; FIG. 11). Interestingly, as shown in FIG. 12, the size of the region where SSBs were identified (peak width of the single-stranded break signal) could be controlled from 500 to 2000 bp dependent on the total amount of dNTPs that were present during the second extension reaction (a reaction performed prior to biotin-mediated pulldown reactions).

Example 3: Sites of Single-Stranded Breaks were Identified Through a Combination of the Engineered Variant Signal and Biotin Enrichment An advantage the two-step incorporation of biotin dUTP and dPTP/dKTP of the instant disclosure offers is two measurements on the location of where DNA damage occurs: (1) In the regions defined by the peaks in sequencing coverage and (2) by the base calls at each position across the reference. The base frequencies outside the regions defined by peaks had low coverage and could result in spurious mutational fractions depending on sequencing noise and were not considered for variant calling analysis. DNA SSBs possess stranded properties in that one strand of the DNA helix contains the original correct base and the other strand (where the nick occurs) contains Ps and Ks. When sequencing libraries for SSBs, theoretically 50% of the bases are called from the correct strand and the remaining from P and K base pair distributions. Since the correct base (majority) was measured, the variant base could then be identified, assuming that a P or K was added at each position (defined as the unexpected base).

Figure 13:
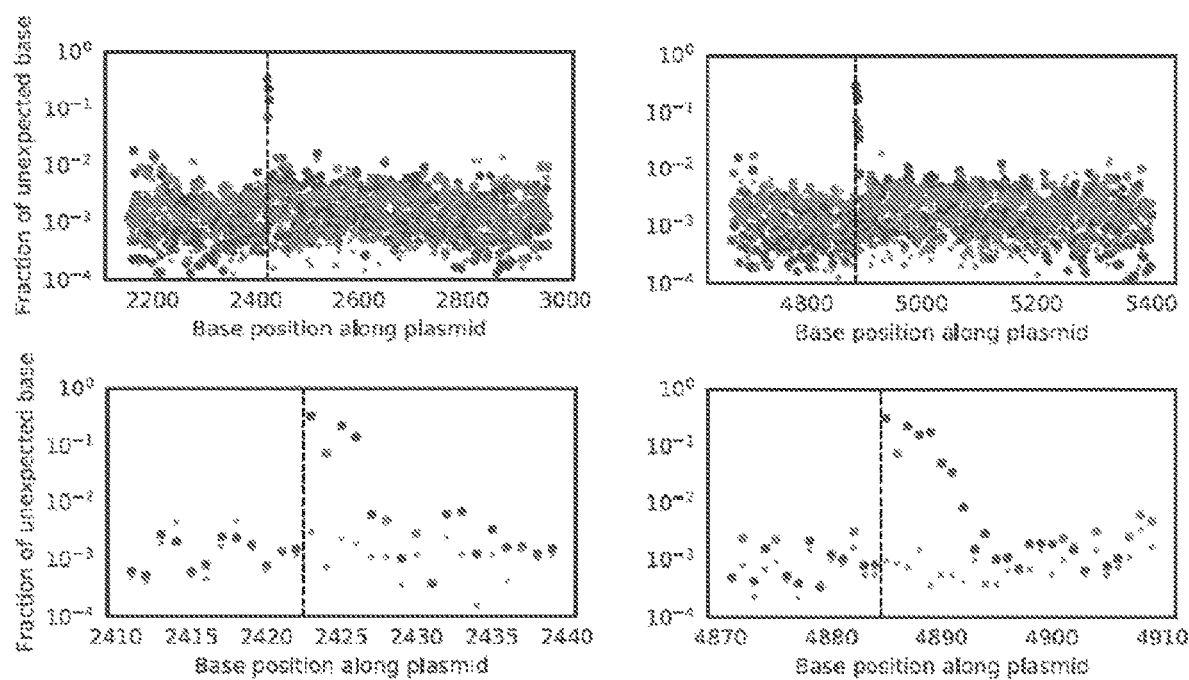
FIG. 13 shows the mutational signature observed at the site of single-stranded breaks. Base mutation frequencies at locations of SSBs are shown in regions with sequencing peaks. The mutated fraction was plotted for the full region of the peaks (top) and a zoomed-in region (bottom). The dashed vertical line indicates the position of the nick. Gray data points represent the mutation frequencies in the no nick control sample. Blue and green data points indicate whether a potential P or K was incorporated at that base position. The unexpected base was the non-reference base that would arise due to PCR with P or K in the template.

In the case where all DNA was nicked, the unexpected base fraction occurred at ~10-30%, whereas the average sequencing noise was 0.1%-1% (FIG. 13). The directionality of extension, and hence the 5' end of the SSB, could be inferred by observing the declining signature of variants where the max expected base frequency occurred directly next to the break (FIG. 13). The decreasing signal and the ultimate number of universal bases added likely reflected the stability of the DNA duplex containing a long string of Ps and Ks (Hill 1998). Alternatively, comparing the location of the sequencing coverage peak to where the mutational signature occurred gave another measure of which strand the break occurred upon (FIG. 9). The combination of enriched sites of DNA SSBs through biotin pulldown and a unique mutational signature from the universal bases rendered the NickSeq process disclosed herein a robust platform for detecting DNA damage.

Figure 14A:
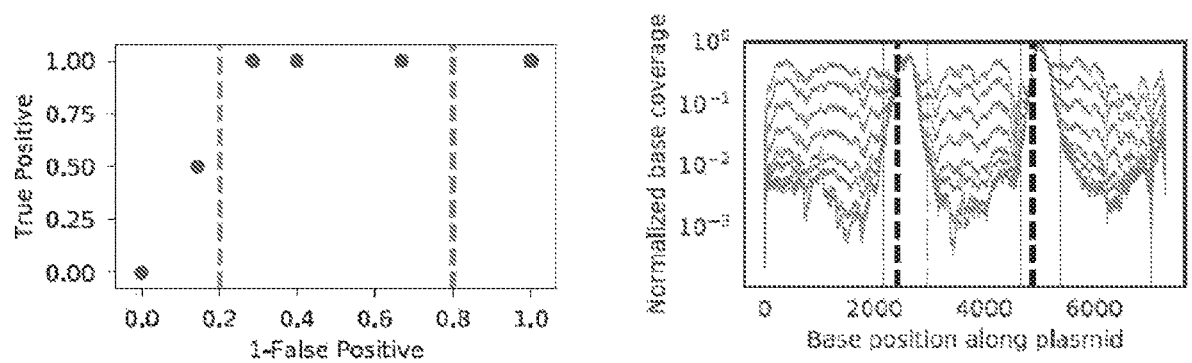
FIGS. 14A and 14B show in silico sensitivity analysis for single-stranded break detection.
Figure 14B:
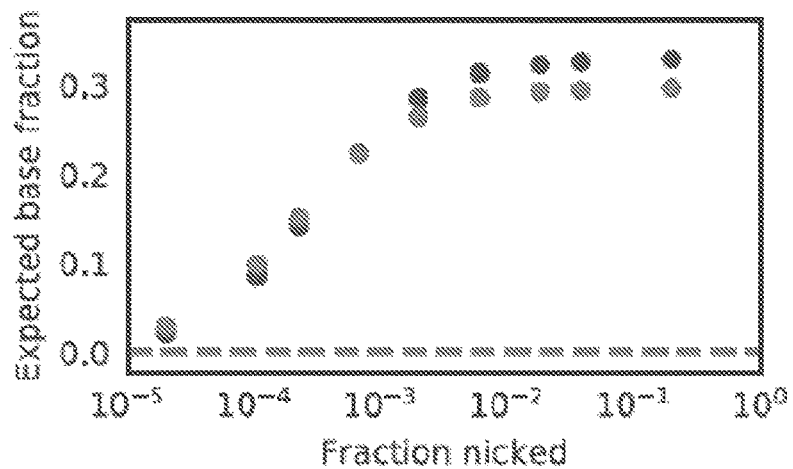

Example 4: In Silico Analysis Revealed the Theoretical Sensitivity of NickSeq as One Nick Per One Thousand Molecules The approximate sensitivity of calling peaks and identifying mutated bases was determined through in silico analysis. Because there are two distinct measurements of SSB sites, the sensitivity of each case was analyzed separately. First, the sensitivity of calling peaks in sequencing coverage was calculated and then the sensitivity of identifying a mutated base at the break position was determined. Background noise was added to the sample containing 100% nicked DNA down to the level of 1 nick out of $10^5$ molecules. A receiver operator characteristic (ROC) was calculated, where the fraction of nicked DNA was thresholded to show that the two known regions of SSBs could be reliably called down to 1 in $10^4$ nicks but false regions started appearing after 1 out of $10^3$ nicks (FIG. 14A). The base frequencies at every position offered an orthogonal measurement of nicked location compared to the sequencing coverage of the reads. An approximate sensitivity on base calling was determined by calculating the decrease in signal at the 5'-most base of the SSB as more noise was added to the data (FIG. 14B). The unexpected base fraction was distinguishable from sequencing noise down to $1/10^5$ nicks. NickSeq therefore offered the first known measurement of the location of SSBs with a sensitivity on the order of 1 out of $10^3$ nicks.

Example 5: "NickSeq" Precisely Identifies Single-Stranded Break Positions in Genomic DNA Genomic DNA (prokaryotic or eukaryotic, optionally mammalian genomic DNA) is obtained and subjected to the "NickSeq" process. Extensive sequencing of "NickSeq" processed dsDNA fragments reveals a number of sites of single-stranded breaks across the genome examined. Location and pattern analysis performed upon such sequences reveals regions of potential single-stranded break "hotspots" across the genome, and performance of the "NickSeq" process (including extensive fragment sequencing) is used to add additional information to a training set and/or as a test set used for validation of potential sites of single-stranded DNA break "hotspots". Experiments are performed as described above for plasmid DNA single-stranded break detection, though replicates become more important to ensure that no DNA breaks are created inadvertently through manual handling. In addition, sequencing depth is increased to cover the entire genome, and it is contemplated that DNA can be treated with repair enzymes to target other types of mutations or repair the 3' OH needed on the nick.

Example 6: "NickSeq" Precisely Identifies Genomic Sites of Off-Target Cas9 Nickase Activity The instant "NickSeq" method can be readily applied to identification of off-target single-stranded break events performed by the Cas9 nickase during use of CRISPR/Cas9 gene editing. While on-target gene editing using CRISPR/Cas9 can be readily identified, any off-target nicking attributable to Cas9 has the potential to induce deleterious effects, yet such off-target events have heretofore been difficult to identify. In vitro determination of off-target Cas9 nickase activity can therefore be performed using the instant "NickSeq" method. Guide strands disclosed in Tsai S Q, et al. Nat Bio. (33) 2015 were previously identified in the art as exhibiting off-target activity, and the instant "NickSeq" methods are employed in the current example to test for Cas9 nickase-mediated off-target effects of guide strands with improved sensitivity of detection and specificity of nick location. The instant methods are therefore employed to optimize use of CRISPR/Cas9 approaches, e.g., in a clinical setting in which off-target effects are to be minimized or avoided.

Example 7: Use of Other DNA Polymerase Enzymes and Degenerate Nucleotides in "NickSeq"

Figure 15A:
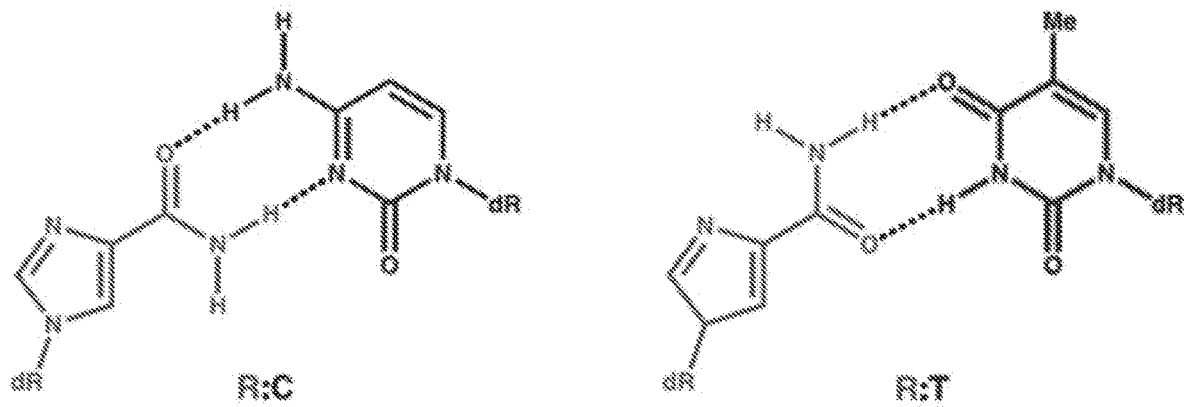
FIGS. 15A and 15B show assessment of dRTP use as a degenerate C/T-binding nucleotide in the "NickSeq" process of the instant disclosure.
Figure 15B:
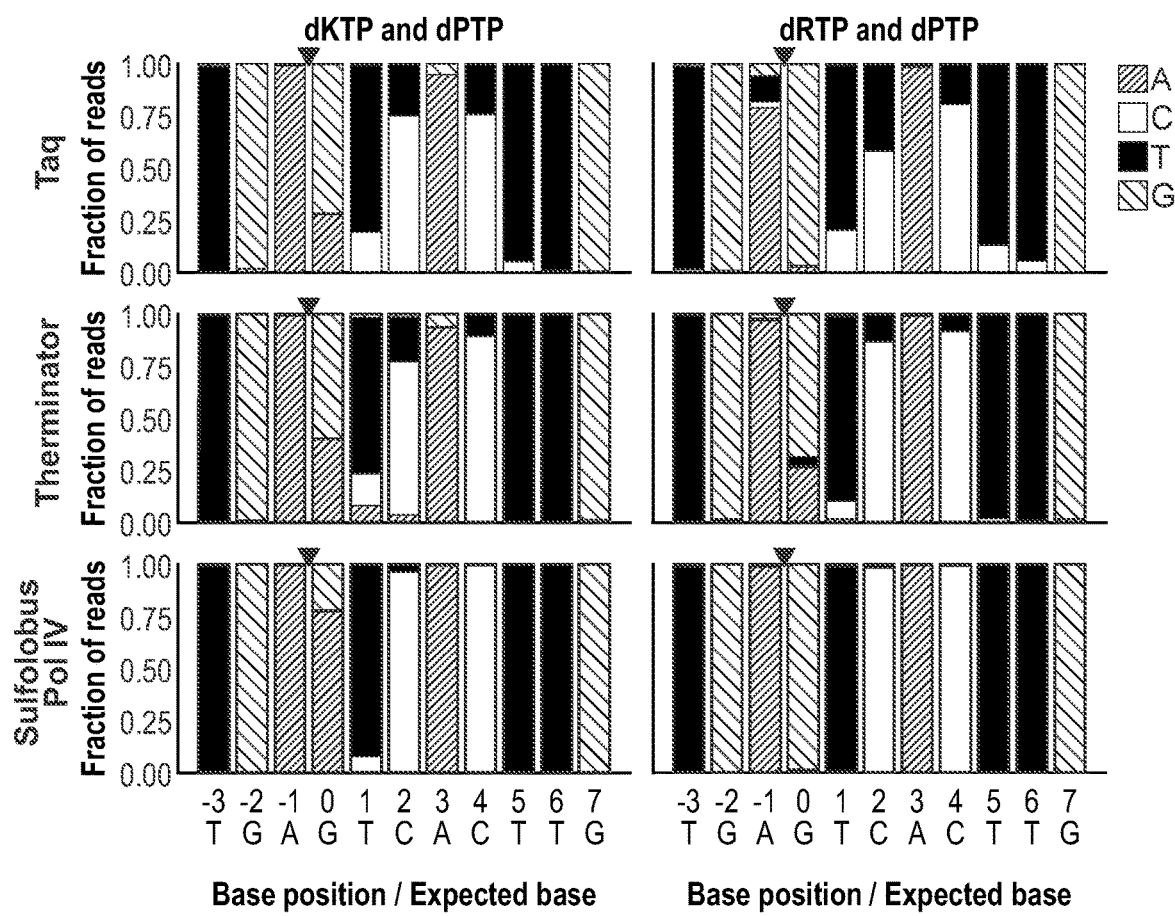

Other DNA polymerase enzymes and an additional degenerate nucleotide, dRTP (deoxy-ribavirin 5'-O-triphosphate), were also assessed for efficacy in the "NickSeq" process, specifically during the initial nick translation step. While dKTP has been described as base pairing with both cytosine (C) and thymine (T) residues, dKTP has also been described as having a strong bias for base pairing with T. dRTP was therefore assessed as a possible replacement for dKTP in the "NickSeq" process of the instant disclosure, in view of dRTP also base pairing with C and T (FIG. 15A) and with the possibility that dRTP might show less bias than dKTP (which could thereby render dRTP a preferred degenerate nucleotide as compared to dKTP, at least for certain applications). Experimental assessment of dRTP identified that, depending upon the DNA polymerase enzyme used during nick translation, use of dRTP led to unanticipated behavior (Taq DNA polymerase (Taq)), regular incorporation but no obvious improvement over using dKTP (Terminator DNA polymerase), or no incorporation at all (*Sulfolobus* DNA polymerase IV) (FIG. 15B).

Figure 16:
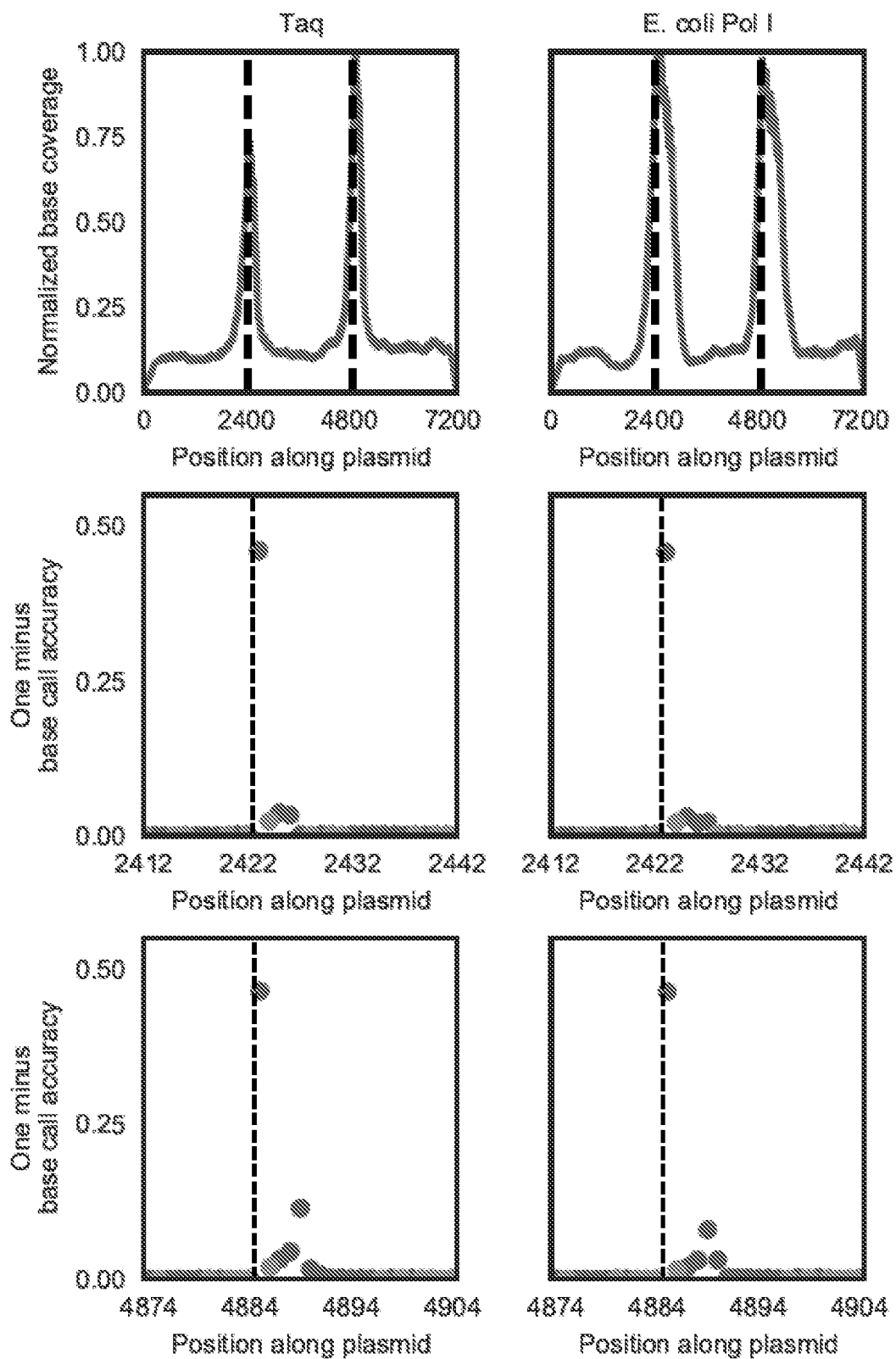
FIG. 16 shows results obtained when the "NickSeq" process of the instant disclosure was performed using *E. Coli* DNA polymerase I (Pol I).

*E. Coli* DNA polymerase I (Pol I) was assessed for use during the second nick translation step of the "NickSeq" process of the instant disclosure, together with regular dNTPs and biotinylated dUTP. As shown in FIG. 16, Pol I did not result in noticeable changes to library enrichment from the streptavidin pulldown or to mutational signal from the degenerate nucleotides as compared to Taq. While the observed peaks in sequencing coverage were wider for Pol I, this facet of Pol I performance can be readily tuned by decreasing the time the DNA is incubated with the polymerase. In view of the observed Pol I performance, it was further noted that use of Pol I would likely be capable of lowering background noise, since Pol I exhibits a lower error rate than Taq (due to the 3'->5' exonuclease proofreading activity of Pol I).

Example 8: Use of Desthiobiotinylated Nucleotides in "NickSeq"

Figure 17A:
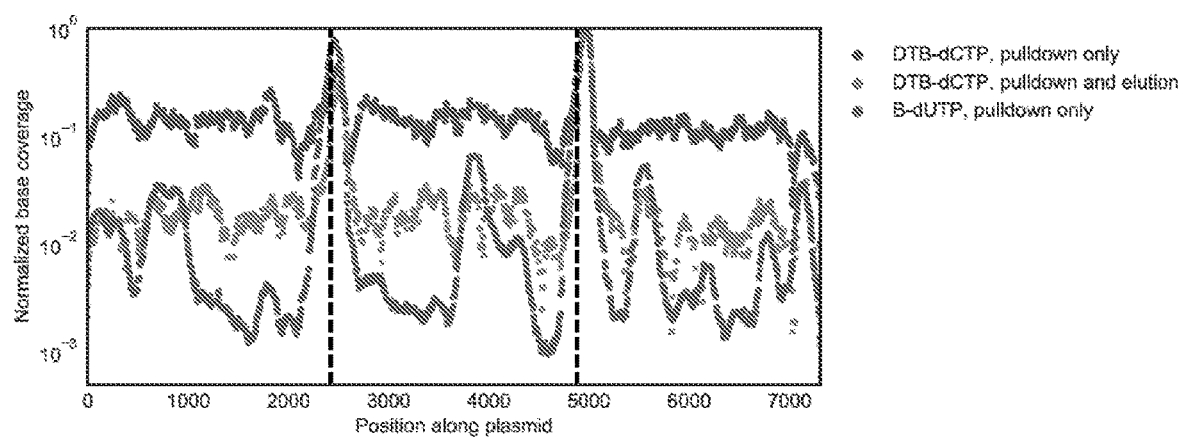
FIGS. 17A and 17B show results of assessing desthiobiotinylated nucleotides for library enrichment in the "NickSeq" process of the instant disclosure, in replacement for biotinylated dUTP.
Figure 17B:
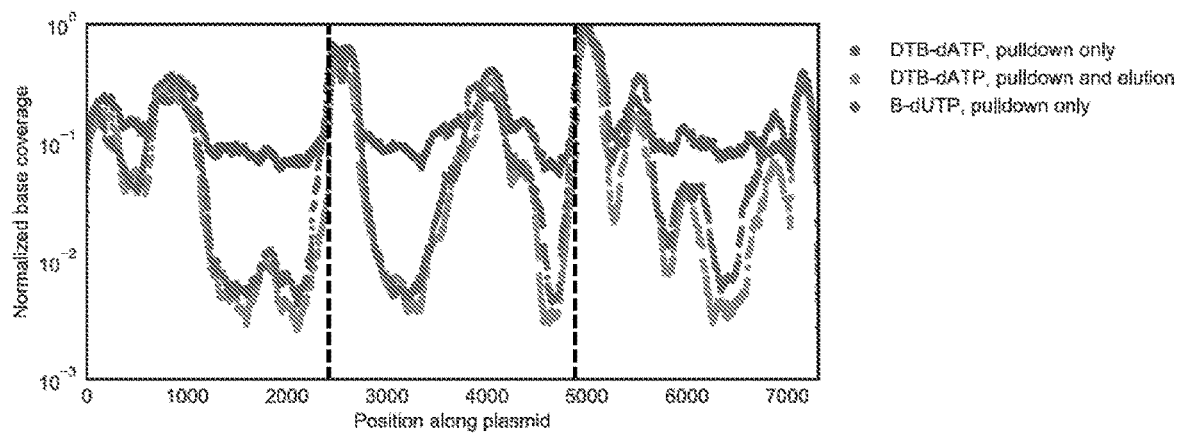

Desthiobiotinylated nucleotides were assessed for library enrichment in the "NickSeq" process of the instant disclosure, in replacement for biotinylated dUTP. In certain of the above Examples, PCR was performed with streptavidin beads in the reaction mix, and after the pulldown step, it would be difficult to separate the biotin from the streptavidin. These beads are known to inhibit PCR at high enough concentrations and attachment of DNA to the beads could potentially prevent polymerase activity if there was steric hindrance. Desthiobiotin binds to streptavidin very tightly ($K_D=10^{-11}$M), but not as tightly as biotin ($K_D=10^{-15}$M). This means that desthiobiotinylated nucleotides can be used for efficient library enrichment and then eluted from the streptavidin beads by competition with free biotin, potentially yielding a more robust result in the "NickSeq" process. While the desthiobiotinylated dCTP tested actually provided worse enrichment than biotinylated dCTP, desthiobiotinylated dATP was observed to provide slightly better enrichment than the original biotinylated dUTP (FIGS. 17A and 17B).

Example 9: Use of Other Heat-Tolerant DNA Polymerase Enzymes in "NickSeq"

Figure 18:
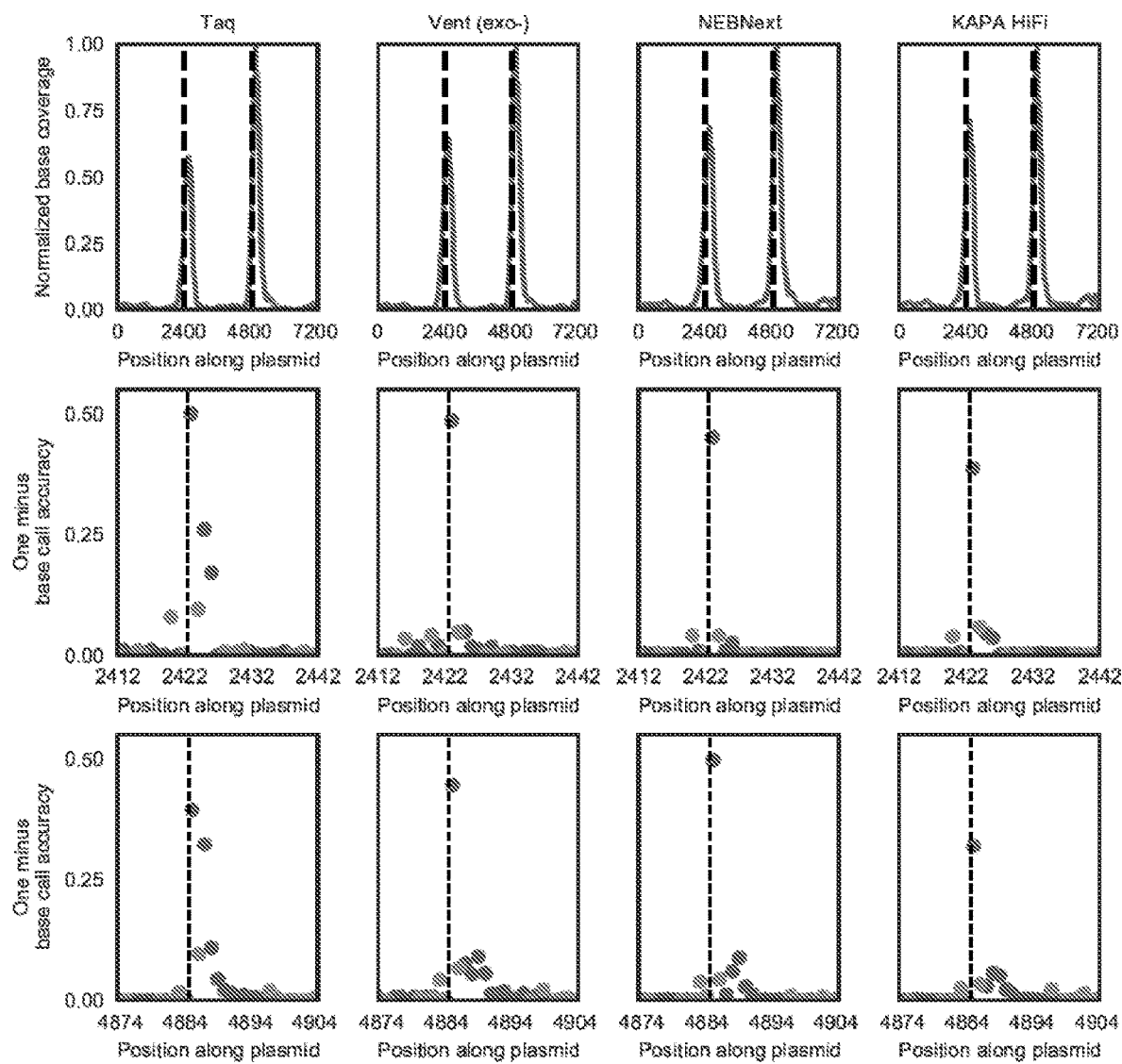
FIG. 18 shows results obtained for three additional heat-tolerant DNA polymerases when tested in the "NickSeq" process of the instant disclosure, in replacement for Taq polymerase.

Three additional heat-tolerant DNA polymerases were tested for use during PCR in the "NickSeq" process of the instant disclosure. As observed in FIG. 18, all three additional heat-tolerant DNA polymerases (Vent® (exo-), NEBNext® and KAPA HiFi™) resulted in similar library enrichments and mutational signals when compared to the original Taq used in certain of the above Examples. (FIG. 18). Vent® (exo-) is a thermostable DNA polymerase that has been genetically engineered to eliminate the 3'→5' proofreading exonuclease activity associated with the thermostable archean Vent® DNA Polymerase. NEBNext® polymerase is high-fidelity thermostable DNA polymerase. KAPA HiFi™ is a high-fidelity thermostable DNA polymerase that has been engineered to have an increased affinity for DNA without the need for accessory protein domains. Some enzymes, specifically KAPA HiFi™, were observed to be better suited for PCR, due to their lower error rates and abilities to amplify lower quantities of starting DNA. Accordingly, replacement of KAPA HiFi™ for Taq has been employed to improve the "NickSeq" process of the instant disclosure.

Figure 19A:
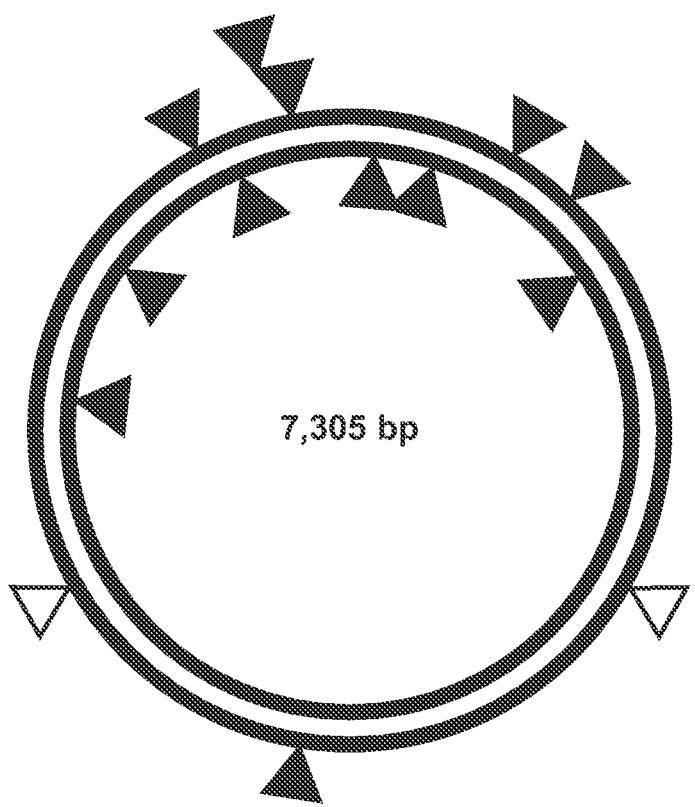
FIGS. 19A to 19D show that the "NickSeq" process of the instant disclosure was able to detect DNA single-strand breaks that occurred in only a small fraction of the DNA molecules present in a sample.
Figure 19B:
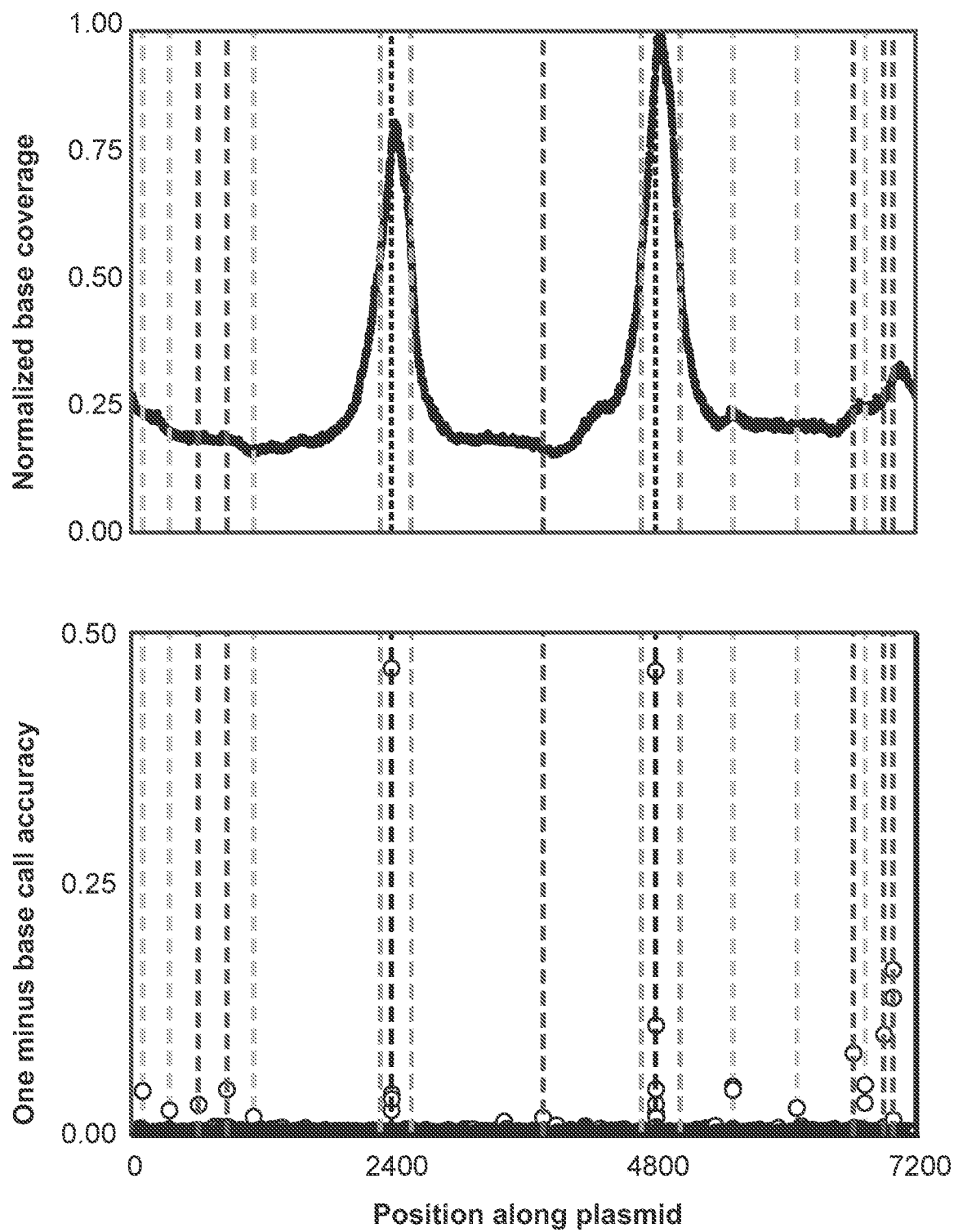

Example 10: Validation of "NickSeq" Sensitivity in Detecting Single-Strand Breaks that Occur in Only a Small Fraction of the DNA Molecules Present in a Sample The ability of the "NickSeq" process of the instant disclosure to detect single-stranded breaks that occur in only a small fraction of DNA molecules present in a sample was further investigated using two different test plasmids and respectively using the Nb.BsmI nicking endonuclease and Cas9 nickase with a guide RNA. When using the nicking endonuclease Nb.BsmI on a plasmid, off-target activity was detected based on NickSeq's mutational signal at multiple locations that contain a one base pair mismatch from the enzyme's target sequence (FIGS. 19A and 19B). Two "NickSeq" base coverage peaks were observed at target sites, while reference and non-reference strand off-target sites also showed certain one minus base call accuracy signals at these locations.

Figure 19C:
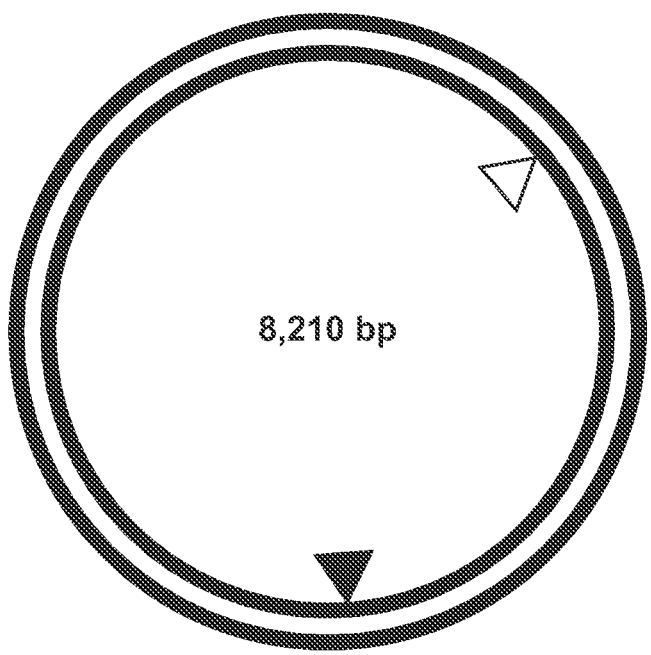
Figure 19D:
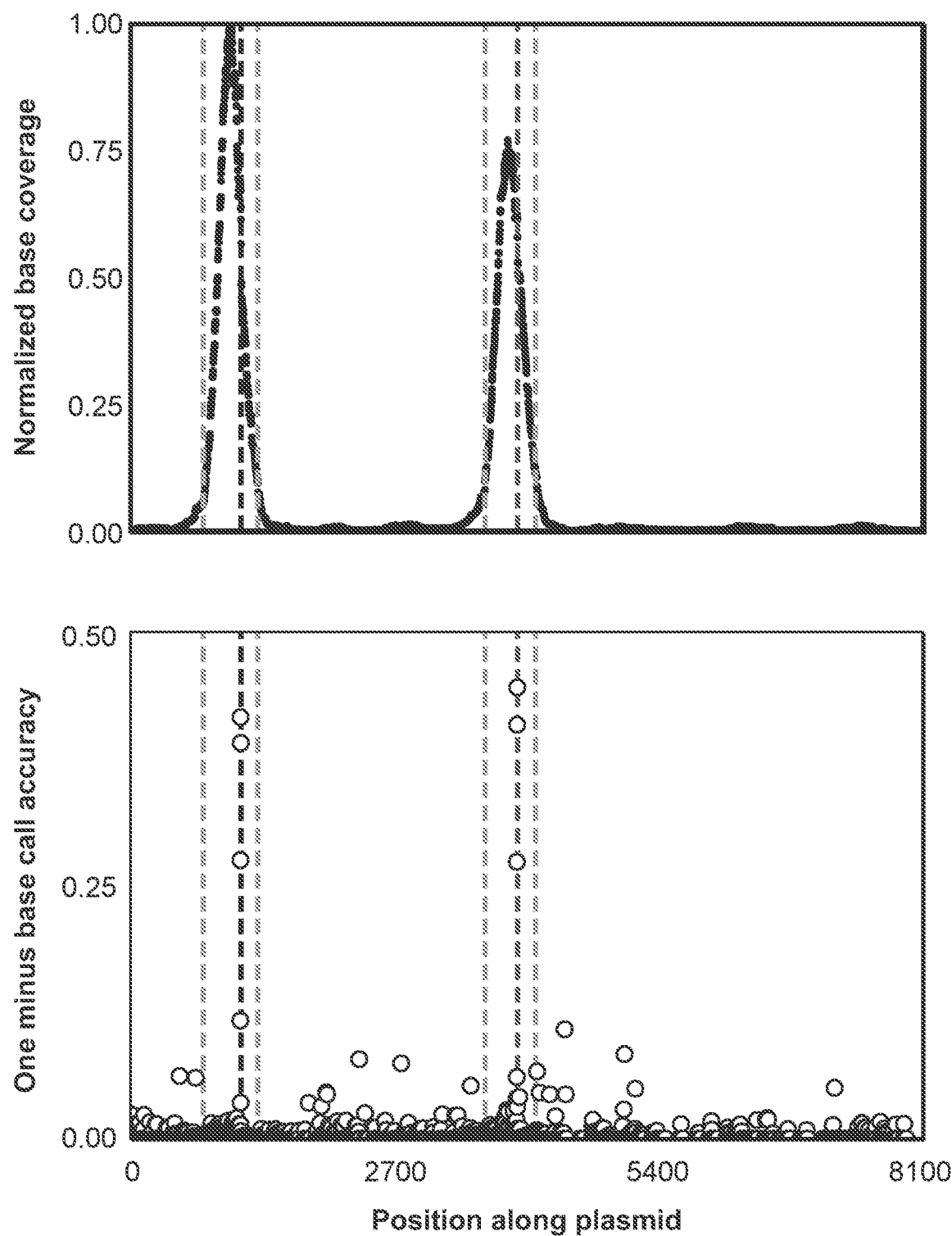

When using Cas9 nickase and a guide RNA on a plasmid, off-target activity was detected based on NickSeq's mutational and library enrichment signals at a location that contains five base pair mismatches from the guide RNA (FIGS. 19C and 19D).

Figure 20A:
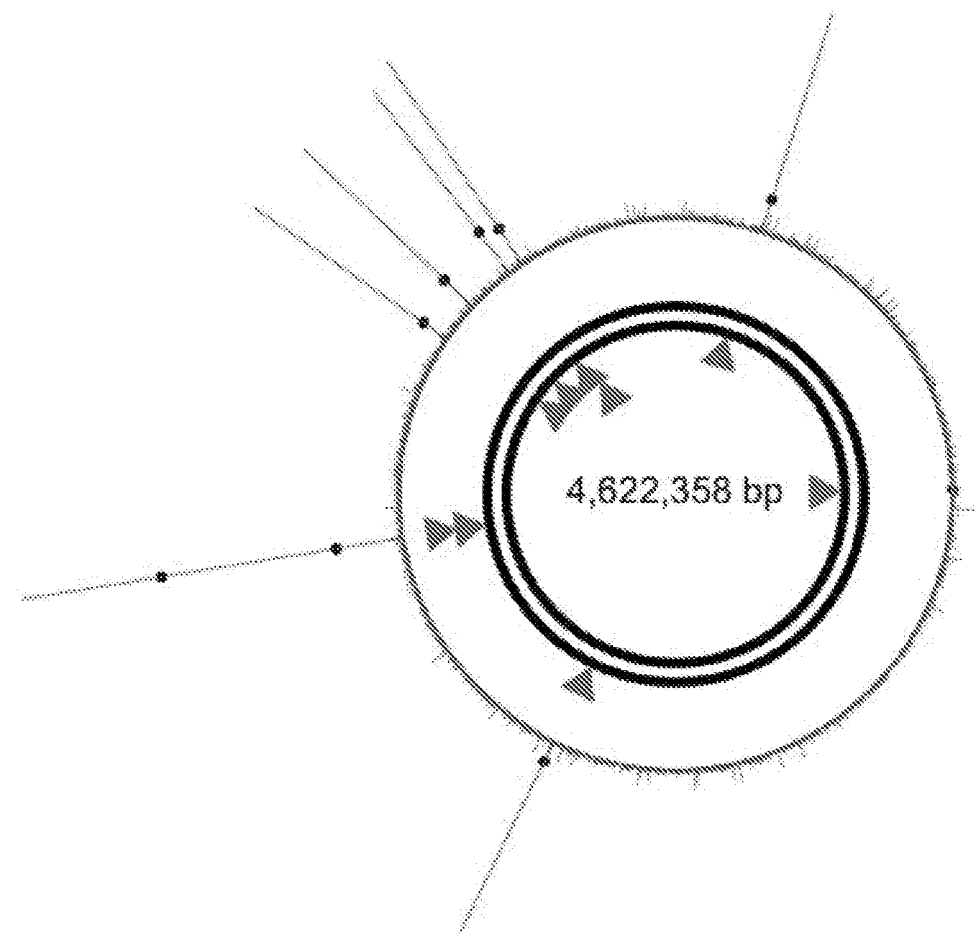
FIGS. 20A to 20D demonstrate successful application of the "NickSeq" process of the instant disclosure to detection of single-strand DNA breaks in a bacterial genome.
Figure 20B:
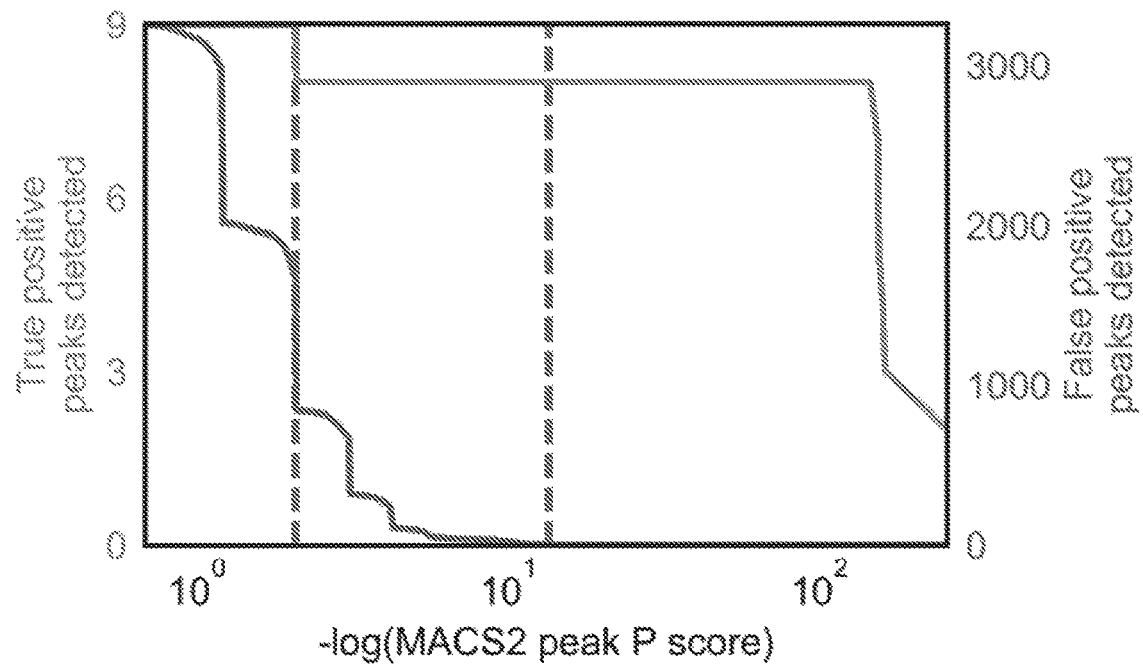

Example 11: Use of "NickSeq" with Longer DNA Molecules and Demonstrated Ability to Detect Single-Strand Breaks in a Bacterial Genome Two guide RNAs in combination with Cas9 nickase were used upon a bacterial genome. One guide RNA targeted eight locations and the other targeted a single location (FIG. 20A). Sequencing coverage alone was observed to be insufficient to identify all single-strand breaks across the tested bacterial genome. Highly penetrant breaks exhibited very high MACs2 peak p values, but the break caused by the second guide RNA was lowly penetrant and numerous background peaks exhibited higher p values (FIG. 20B).

Figure 20C:
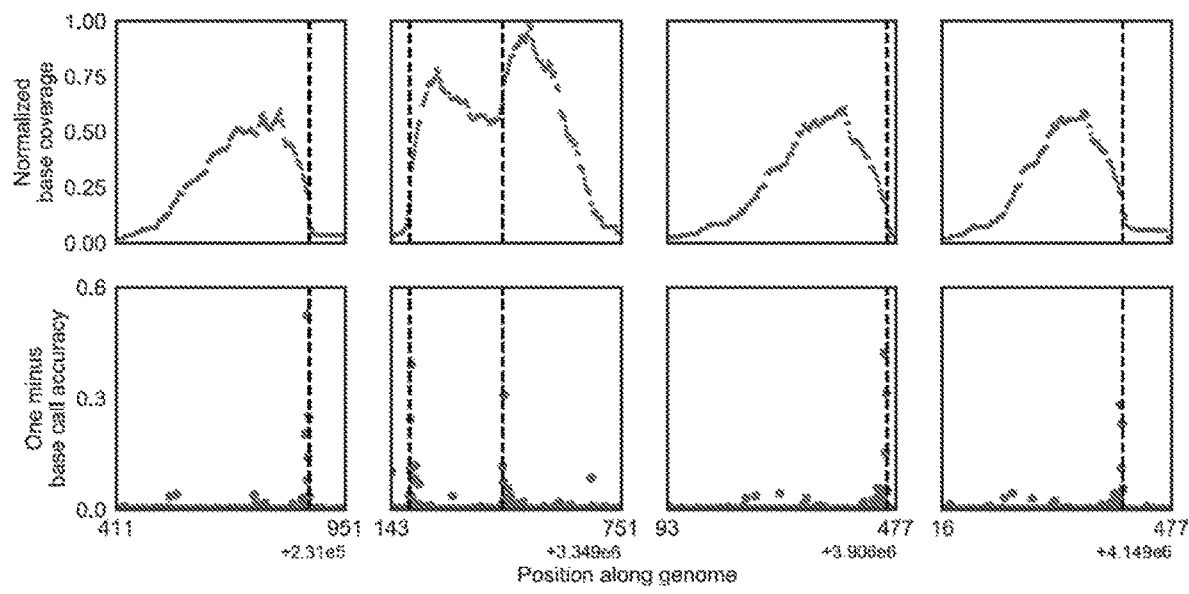
Figure 20D:
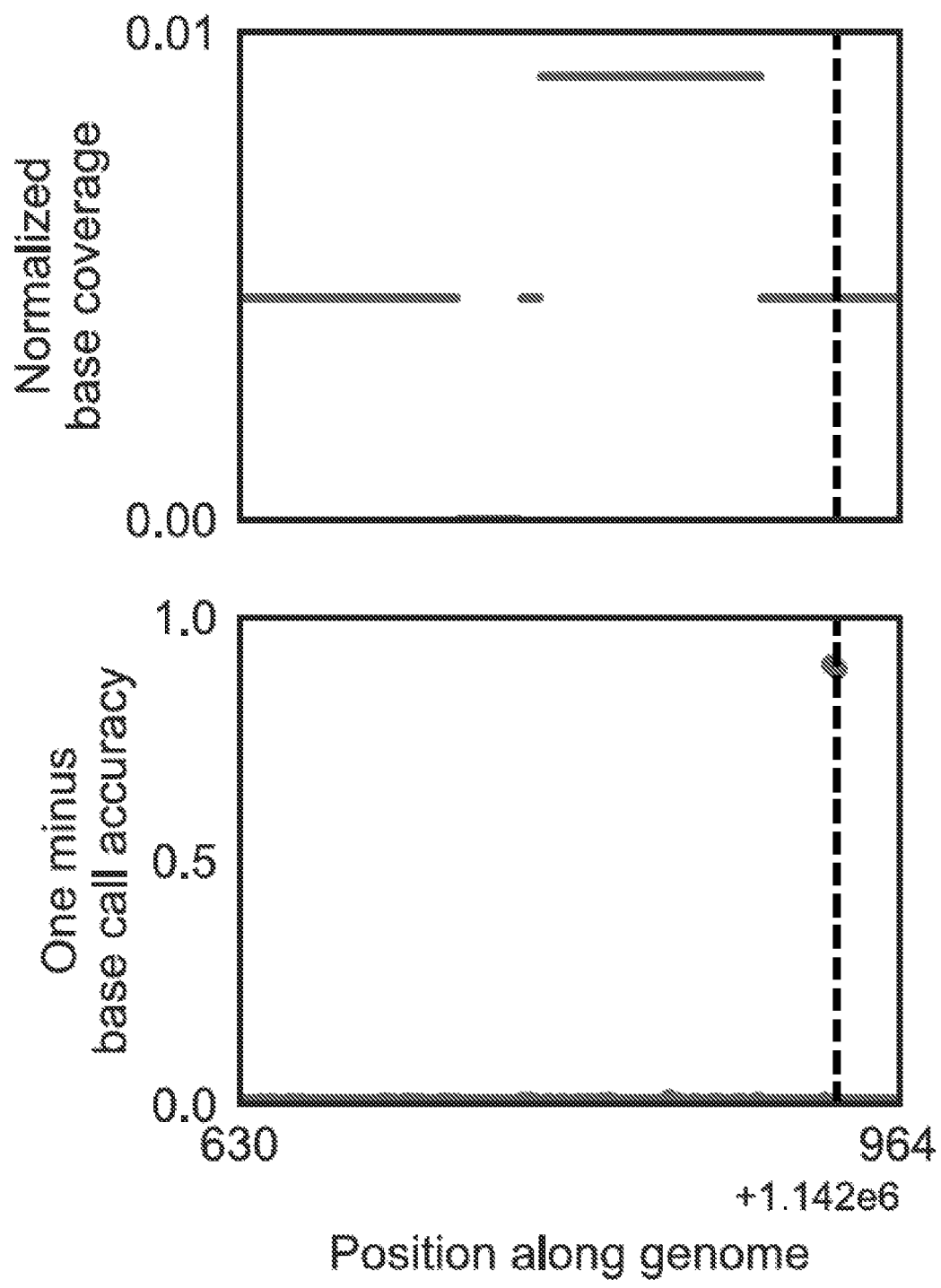
Figure 21:
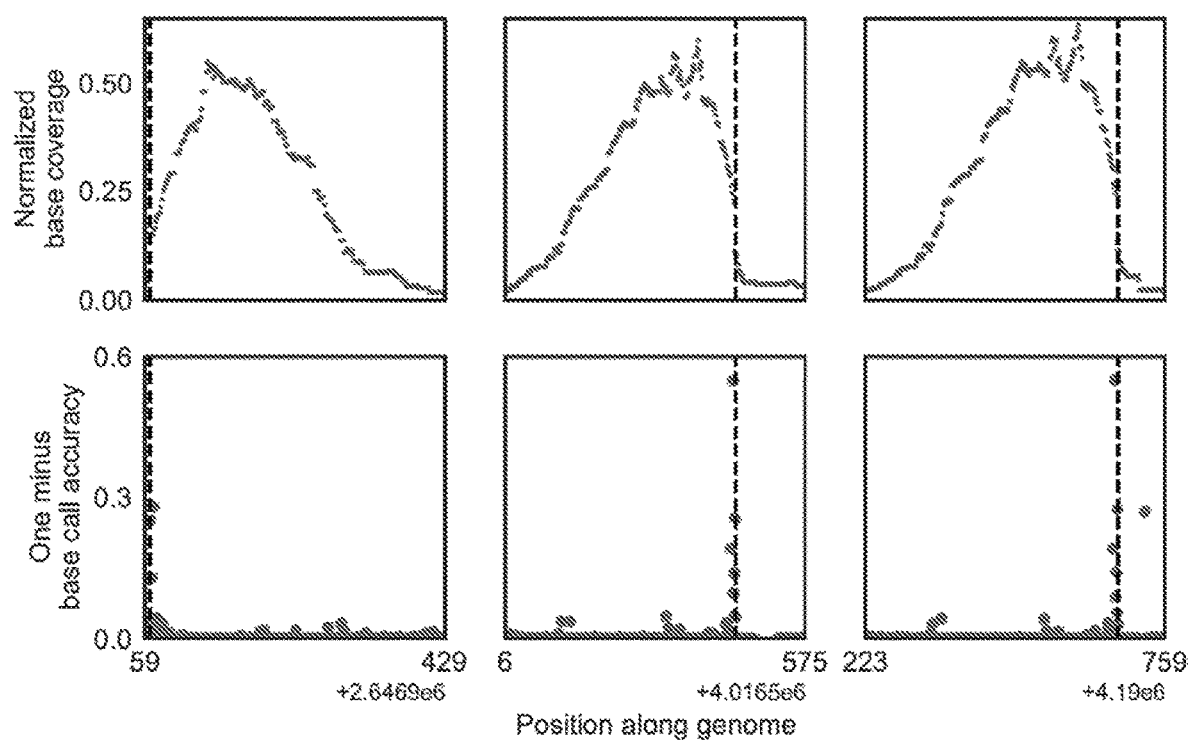
FIG. 21 shows "NickSeq" results demonstrating single-strand break detection in a bacterial genome at single nucleotide resolution.

The eight breaks caused by the first guide RNA were all identified with single nucleotide resolution by the "NickSeq" process of the instant disclosure (FIGS. 20C and 21). The lone break caused by the second guide RNA was also identified; yet identification of this lone break required the mutational signal unique to the "NickSeq" process of the instant disclosure (FIG. 20D). For all detected single-strand breaks, the strandedness of the break could also be determined by comparing the break location to the location of maximum sequencing coverage within the peak.

Figure 22:
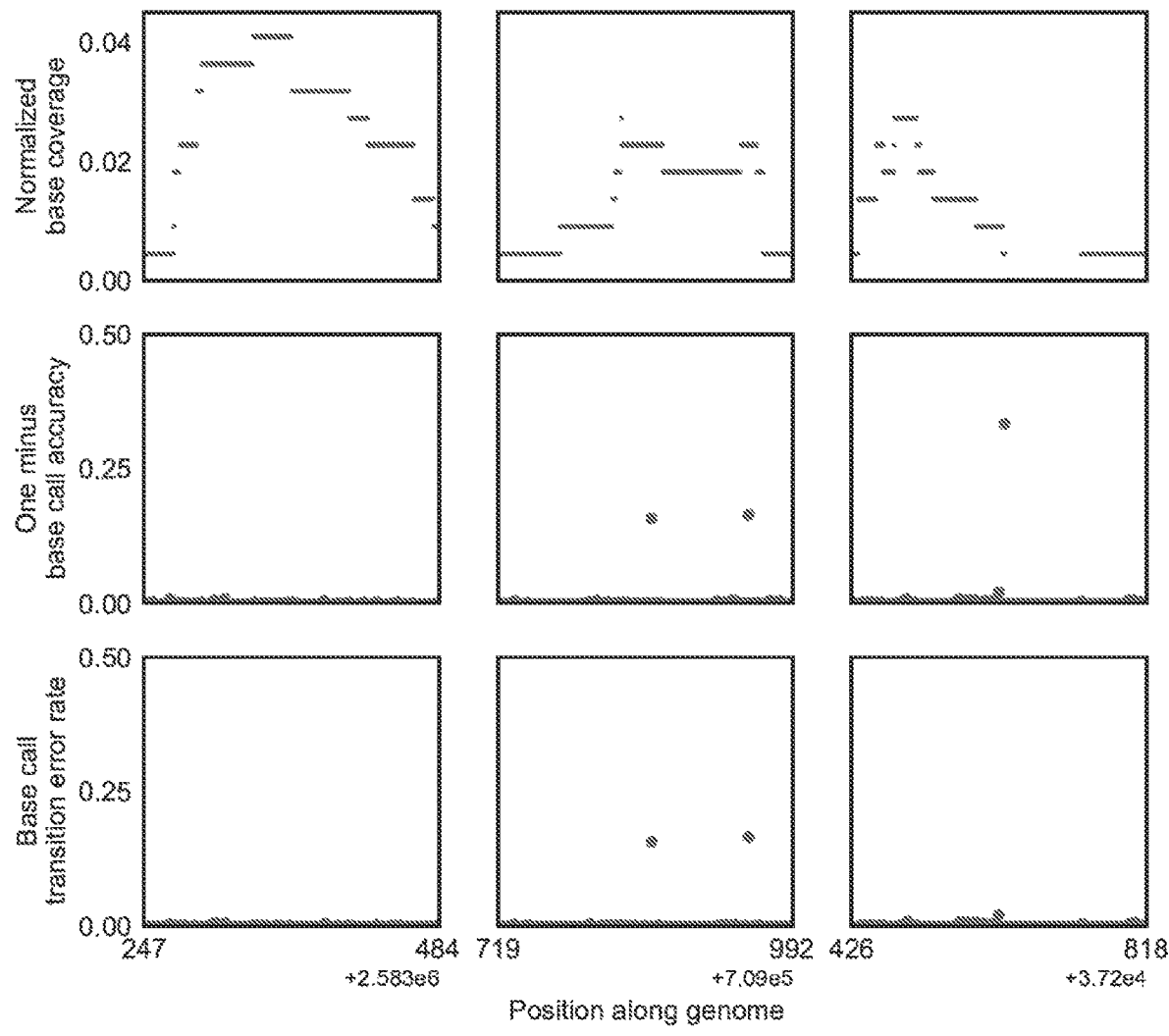
FIG. 22 shows "NickSeq" detection of mutational signal in a bacterial genome, where the "NickSeq" signal was capable of excluding peaks that did not contain any mutational signal, or contained signal but not at consecutive nucleotides (as would be expected from addition of multiple dPTP and dKTP at a break), or contained a mutational signal but not one that could be caused by dPTP and dKTP (C↔T and A↔G).

MACs2 peak p values and other metrics based on sequencing coverage were insufficient to filter out all peaks; however, the mutational signal could still be identified. Many peaks either did not contain any mutational signal, or contained signal but not at consecutive nucleotides (as would be expected from addition of multiple dPTP and dKTP at a break), or contained a mutational signal but not one that could be caused by dPTP and dKTP (C↔T and A↔G) (FIG. 22).

REFERENCES

Yan, W. BLISS is a versatile and quantitative method for genome-wide profiling of DNA double-strand breaks.
Crosetto N. Nucleotide-resolution DNA double-strand break mapping by next-generation sequencing.
Lensing. DSBCapture: in situ capture and sequencing of DNA breaks.
Baranello. DNA Break Mapping Reveals Topoisomerase II Activity Genome-Wide.
Kim. Genome-wide target specificities of CRISPR RNA-guided programmable deaminases.
Caldecott. Single-strand break repair and genetic disease.
Bradley. X-ray induced DNA double strand break production and repair in mammalian cells as measured by neutral filter elution.

Higo. DNA single-strand break-induced DNA damage response causes heart failure.

Takashima. Mutation of TDP1, encoding a topoisomerase I-dependent DNA damage repair enzyme, in spinocerebellar ataxia with axonal neuropathy.

Tsai. GUIDE-seq enables genome-wide profiling of off-target cleavage by CRISPR-Cas nucleases.

Hu. Detecting DNA double-stranded breaks in mammalian genomes by linear amplification-mediated high-throughput genome-wide translocation sequencing.

Tsai. CIRCLE-seq: a highly sensitive in vitro screen for genome-wide CRISPR-Cas9 nuclease off-targets.

Date. Early-onset ataxia with ocular motor apraxia and hypoalbuminemia is caused by mutations in a new HIT superfamily gene.

Moreira. The gene mutated in ataxia-ocular apraxia 1 encodes the new HIT/Zn-finger protein aprataxin.

Rigby. Labeling deoxyribonucleic acid to high specific activity in vitro by nick translation with DNA polymerase I.

McKenna The Genome Analysis Toolkit: A MapReduce framework for analyzing next-generation DNA sequencing data.

Li Toward better understanding of artifacts in variant calling from high-coverage samples.

Nassour Defective DNA single-strand break repair is responsible for senescence and neoplastic escape of epithelial cells.

Mellon. Selective removal of transcription-blocking DNA damage from the transcribed strand of the mammalian DHFR gene.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The specific embodiments described herein are not limiting.

The inventors expect skilled artisans to employ variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for identifying the presence and position of a single-stranded break within a double-stranded nucleic acid, the method comprising:

obtaining a sample comprising a double-stranded nucleic acid;

contacting the sample with a DNA polymerase and a nucleotide analog that possesses the ability to base pair with at least two nucleotide bases selected from the group consisting of adenine, guanine, cytosine and thymine, under conditions that allow for the DNA polymerase extension and incorporation of the nucleotide analog to occur, to provide extended double-stranded nucleic acids comprising the nucleotide analog;

contacting the extended double-stranded nucleic acids with a tagged nucleotide and natural deoxyribonucleotides under conditions that allow for a DNA polymerase extension and incorporation of the tagged nucleotide and natural deoxyribonucleotides to occur, to provide tagged extended double-stranded nucleic acids;

fragmenting the tagged extended double-stranded nucleic acid in the sample, thereby producing a population of tagged double-stranded nucleic acid fragments;

isolating tagged double-stranded nucleic acid fragments from the population of double-stranded nucleic acid fragments;

ligating an exogenous oligonucleotide sequence to the isolated tagged double-stranded nucleic acid fragments;

amplifying the isolated tagged double-stranded nucleic acid fragments comprising the exogenous oligonucleotide sequence, thereby forming an amplified population of isolated double-stranded nucleic acid fragments;

identifying nucleotide sequences of the amplified population of isolated double-stranded nucleic acid fragments; and within a nucleotide sequence obtained from the amplified population of isolated double-stranded nucleic acid fragments, identifying a series of three or more consecutive nucleotide positions that have at least two or more detectable nucleotide residues present at a level of at least 10% of all nucleotide residues detected at that position, at each of the three or more consecutive nucleotide positions, thereby identifying the presence and position of a single-stranded break within a double stranded nucleic acid.

2. The method of claim 1, wherein the nucleotide analog is selected from the group consisting of dPTP, dKTP, dRTP, inosine, 3-Nitropyrrole, 5-nitroindole, 3-methyl isocarbostyril (MICS), 5-methyl isocarbostyril (5MICS), and 3-methyl 7-propynyl isocarbostyril (PIM).

3. The method of claim 1, wherein the sample comprising a double-stranded nucleic acid is contacted with two or more nucleotide analogs that each possesses the ability to base pair with at least two nucleotide bases selected from the group consisting of adenine, guanine, cytosine, and thymine.

4. The method of claim 1, wherein the DNA polymerase is selected from the group consisting of Taq DNA polymerase, Therminator DNA polymerase and *Sulfolobus* DNA polymerase IV.

5. The method of claim 1, wherein the DNA polymerase is a DNA polymerase I.

6. The method of claim 1, wherein the tagged nucleotide is a biotin-labeled nucleotide or a desthiobiotin-labeled nucleotide.

7. The method of claim 6, wherein the isolating step comprises contacting tagged double-stranded nucleic acid fragments comprising the biotin-labeled or desthiobiotin-labeled nucleotides with streptavidin.

8. The method of claim 1, wherein the fragmenting step produces a population of tagged double-stranded nucleic acid fragments having an average fragment size of 20-2000 base pairs, or 200-700 base pairs.

9. The method of claim 1, wherein the sample comprising a double-stranded nucleic acid comprises a prokaryotic double-stranded nucleic acid, or a prokaryotic double-stranded nucleic acid genome.

10. The method of claim 1, wherein the sample comprising a double-stranded nucleic acid comprises a eukaryotic double-stranded nucleic acid, a mammalian genome, or a mammalian genome that has been subjected to a CRISPR/Cas9 procedure.

11. The method of claim 1, wherein the DNA polymerase of the step of contacting the sample with a tagged nucleotide and natural deoxyribonucleotides under conditions that allow for DNA polymerase extension and incorporation of the tagged nucleotide and natural deoxyribonucleotides to occur is an *E. coli* DNA polymerase.

12. The method of claim 1, wherein the step of amplifying the isolated tagged double-stranded nucleic acid fragments comprises use of a thermostable DNA polymerase.

13. A method for detecting a single-stranded break hotspot in a genome, the method comprising:

obtaining a sample comprising genomic double-stranded nucleic acid of one or more organisms;

contacting the with a DNA polymerase and a nucleotide analog that possesses the ability to base pair with at least two nucleotide bases selected from the group consisting of adenine, guanine, cytosine and thymine, under conditions that allow for the DNA polymerase extension and incorporation of the nucleotide analog to occur, to provide extended double-stranded nucleic acids comprising the nucleotide analog;

contacting the extended double-stranded nucleic acids with a tagged nucleotide and natural deoxyribonucleotides under conditions that allow for a DNA polymerase extension and incorporation of the tagged nucleotide and natural deoxyribonucleotides to occur, to provide tagged extended double-stranded nucleic acids;

fragmenting the tagged extended double-stranded nucleic acid in the sample, thereby producing a population of tagged double-stranded nucleic acid fragments;

isolating tagged double-stranded nucleic acid fragments from the population of double-stranded nucleic acid fragments;

ligating an exogenous oligonucleotide sequence to the isolated tagged double-stranded nucleic acid fragments;

amplifying the isolated tagged double-stranded nucleic acid fragments comprising the exogenous oligonucleotide sequence, thereby forming an amplified population of isolated double-stranded nucleic acid fragments;

identifying nucleotide sequences of the amplified population of isolated double-stranded nucleic acid fragments;

within a number of sequences obtained from the amplified population of isolated double-stranded nucleic acid fragments, identifying in each sequence a series of three or more consecutive nucleotide positions that have at least two or more detectable nucleotide residues present at a level of at least 10% of all nucleotide residues detected at that position, at each of the three or more consecutive nucleotide positions, thereby identifying the presence and position of single-stranded breaks within a double stranded nucleic acid; and identifying at least two of the number of sequences as having the same position of single stranded break, thereby identifying the presence and position of a single-stranded break hotspot within a genomic double-stranded nucleic acid.

14. The method of claim 13, wherein:

the step of identifying at least two of the number of sequences as having the same position of single stranded break comprises comparing the presence and position of a first single-stranded break within a genomic double-stranded nucleic acid of an organism with the position of a second single-stranded break within a genomic double-stranded nucleic acid of an organism; and if the sites of the first and second single-stranded breaks are the same and occur at a prevalence that is significantly more than chance, identifying the location of the first and second single-stranded break as a single-stranded break hotspot in the genome of the organism;

the one or more organisms comprise at least one bacteria-bacterium;

the one or more organisms comprise at least one eukaryote;

the one or more organisms have been contacted with an agent or a mutagenic agent;

the one or more organisms have been contacted with a therapeutic agent, is a chemotherapeutic agent, or an antibiotic;

the one or more organisms have been exposed to an altered environmental condition;

the nucleotide analog is selected from the group consisting of dPTP, dKTP, dRTP, inosine, 3-Nitropyrrole, 5-nitroindole, 3-methyl isocarbostyril (MICS), 5-methyl isocarbostyril (5MICS), and 3-methyl 7-propynyl isocarbostyril (PIM);

the sample comprising a double-stranded nucleic acid is contacted with two or more nucleotide analogs that each possesses the ability to base pair with at least two nucleotide bases selected from the group consisting of adenine, guanine, cytosine, thymine, dPTP, dKTP, -dPTP, and dRTP;

the tagged nucleotide is a biotin-labeled nucleotide or a desthiobiotin-labeled nucleotide;

the fragmenting step produces a population of double-stranded nucleic acid fragments having an average fragment size of 20-2000 base pairs, or 200-700 base pairs;

the DNA polymerase is selected from the group consisting of Taq DNA polymerase, Therminator DNA polymerase and *Sulfolobus* DNA polymerase IV;

the DNA polymerase is a DNA polymerase I;

the DNA polymerase of the step of contacting the sample with a tagged nucleotide and natural deoxyribonucleotides under conditions that allow for DNA polymerase extension and incorporation of the tagged nucleotide and natural deoxyribonucleotides to occur is *E. coli* DNA polymerase; and/or the step of amplifying the isolated double-stranded nucleic acid fragments comprises use of a thermostable DNA polymerase.

15. The method of claim 1, wherein the double-stranded nucleic acid is a plasmid.

16. A method for detecting off-target Cas9 nicking activity comprising:

administering Cas9 to a mammalian cell;

obtaining a double-stranded nucleic acid sample from the mammalian cell;

contacting the double-stranded nucleic acid sample with a DNA polymerase and a nucleotide analog that possesses the ability to base pair with at least two nucleotide bases selected from the group consisting of adenine, guanine, cytosine and thymine, under conditions that allow for the DNA polymerase extension and incorporation of the nucleotide analog to occur, to provide extended double-stranded nucleic acids comprising the nucleotide analog;

contacting the extended double-stranded nucleic acids with a tagged nucleotide and natural deoxyribonucleotides under conditions that allow for the DNA polymerase extension and incorporation of the tagged nucleotide and natural deoxyribonucleotides to occur, to provide tagged extended double-stranded nucleic acids;

fragmenting the tagged extended double-stranded nucleic acid in the sample, thereby producing a population of tagged double-stranded nucleic acid fragments;

isolating tagged double-stranded nucleic acid fragments from the population of double-stranded nucleic acid fragments;

ligating an exogenous oligonucleotide sequence to the isolated tagged double-stranded nucleic acid fragments;

amplifying the isolated tagged double-stranded nucleic acid fragments comprising the exogenous oligonucleotide sequence, thereby forming an amplified population of isolated double-stranded nucleic acid fragments;

identifying nucleotide sequences of the amplified population of isolated double-stranded nucleic acid fragments;

within an identified nucleotide sequence of the amplified population of isolated double-stranded nucleic acid fragments, identifying a series of three or more consecutive nucleotide positions that have at least two or more detectable nucleotide residues present at a level of at least 10% of all nucleotide residues detected at that position, at each of the three or more consecutive nucleotide positions, thereby identifying a presence and position of a single-stranded break within a double stranded nucleic acid; and comparing the position of the single-stranded break with a predicted position of Cas9 activity in the mammalian cell, wherein if the position of the single-stranded break differs from the predicted position of Cas9 activity in the mammalian cells, thereby identifying the single-stranded break as a site of off-target Cas9 nicking activity, thereby detecting off-target Cas9 nicking activity in the mammalian cell.

17. The method of claim 16, wherein the nucleotide analog is selected from the group consisting of dPTP, dKTP, dRTP, inosine, 3-Nitropyrrole, 5-nitroindole, 3-methyl isocarbostyril (MICS), 5-methyl isocarbostyril (5MICS) and 3-methyl 7-propynyl isocarbostyril (PIM).

18. The method of claim 16, wherein the double-stranded nucleic acid sample is contacted with two or more nucleotide analogs that each possesses the ability to base pair with at least two nucleotide bases selected from the group consisting of adenine, guanine, cytosine and thymine.

19. The method of claim 18, wherein the two or more nucleotide analogs comprise dPTP and dKTP or dPTP and dRTP.

20. The method of claim 16, wherein the DNA polymerase is selected from the group consisting of Taq DNA polymerase, Therminator DNA polymerase and *Sulfolobus* DNA polymerase IV.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(14)
<223> OTHER INFORMATION: n is dPTP or dKTP

<400> SEQUENCE: 1
cgcaggnnnn nnnnctccgc                                        20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
gcggaggggg aatgcctgcg                                        20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
cgcaggcatt cccctccgc                                         20

<210> SEQ ID NO 4
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(14)
<223> OTHER INFORMATION: n is dPTP or dKTP

<400> SEQUENCE: 4
gcggagnnnn nnnncctgcg                                        20

<210> SEQ ID NO 5
<211> LENGTH: 11
<212> TYPE: DNA
<213> ORGANISM: Artificial
<220> FEATURE:
<223> OTHER INFORMATION: Synthetic

<400> SEQUENCE: 5
tgagtcactt g                                                 11
```